(12) United States Patent
Yang et al.

(10) Patent No.: US 11,207,289 B2
(45) Date of Patent: Dec. 28, 2021

(54) USE OF BENZOFURAN LIGNANS TO INDUCE IL-25 EXPRESSION AND SUPPRESS MAMMARY TUMOR METASTASIS

(71) Applicant: ACADEMIA SINICA, Taipei (TW)

(72) Inventors: Ning-Sun Yang, New Taipei (TW); Yueh-Hsiung Kuo, Taipei (TW); Shu-Yi Yin, New Taipei (TW); Yung-Hsiang Chen, Tainan (TW)

(73) Assignee: ACADEMIA SINICA, Taipei (TW)

( * ) Notice: Subject to any disclaimer, the term of this patent is extended or adjusted under 35 U.S.C. 154(b) by 443 days.

(21) Appl. No.: 16/087,093

(22) PCT Filed: Mar. 17, 2017

(86) PCT No.: PCT/US2017/022948
§ 371 (c)(1),
(2) Date: Sep. 20, 2018

(87) PCT Pub. No.: WO2017/165218
PCT Pub. Date: Sep. 28, 2017

(65) Prior Publication Data
US 2020/0289454 A1 Sep. 17, 2020

Related U.S. Application Data

(60) Provisional application No. 62/311,077, filed on Mar. 21, 2016.

(51) Int. Cl.
*A61K 31/343* (2006.01)
*A61P 35/04* (2006.01)
*A61K 31/337* (2006.01)

(52) U.S. Cl.
CPC .......... *A61K 31/343* (2013.01); *A61K 31/337* (2013.01); *A61P 35/04* (2018.01)

(58) Field of Classification Search
CPC ...... A61K 31/343; A61K 31/337; A61P 35/04
See application file for complete search history.

(56) References Cited

FOREIGN PATENT DOCUMENTS

| TW | 201643148 A | 12/2016 |
|---|---|---|
| WO | 2008062466 A2 | 5/2008 |

OTHER PUBLICATIONS

Mombelli et al. (Scientific Reports 5:11874, 2015).*
Pan, C.-H. et al., "K20E, an oxidative-coupling compound of methyl caffeate, exhibits anti-angiogenic activities through down-regulations of VEGF and VEGF receptor-2", Toxicology and Applied Pharmacology, 2015, vol. 282, pp. 215-226.
Van Miert, S. et al., "Antileishmanial activity, cytotoxicity and QSAR analysis of synthetic dihydrobenzofuran lignans and related benzofurans", Bioorganic & Medicinal Chemistry, 2005, vol. 13, No. 3, pp. 661-669.
Pieters, L. et al., "Synthesis and biological evaluation of dihydrobenzofuran lignans and related compounds as potential antitumor agents that inhibit tubulin polymerization", Journal of Medicinal Chemistry, 1999, vol. 42, No. 26, pp. 5475-5481.
Yin, S.-Y. et al., "Induction of IL-25 secretion from tumour-associated fibroblasts suppresses mammary tumour metastasis", Nature Communications, Apr. 18, 2016, vol. 7, Article No. 11311, internal pp. 1-13.
Apers, S. et al., "Antiangiogenic Activity of Synthetic Dihydrobenzofuran Lignans", J. Nat. Prod., 2002, 65(5), pp. 718-720.
International Search Report of PCT Patent Application No. PCT/US2017/022948 dated Jun. 29, 2017.

* cited by examiner

*Primary Examiner* — Shirley V Gembeh

(57) ABSTRACT

A method for suppressing tumor metastasis, in which an effective amount of a compound of formula (I) is administered to a subject in need thereof. Also disclosed is a method of treating cancer, in which an effective amount of a chemotherapy agent and an effective amount of a compound of formula (I) is administered to a subject in need thereof. Further disclosed are pharmaceutical compositions for suppressing tumor metastasis and for treating cancer, each of the compositions containing a compound of formula (I).

17 Claims, 14 Drawing Sheets

Caffeic acid methyl ester

Methyl (E)-3-[2-(3,4-dihydroxyphenyl)-7-hydroxy-3-methoxycarbonyl-2,3-dihydro-1-benzofuran-5yl]prop-2-enoate

USE OF BENZOFURAN LIGNANS TO INDUCE IL-25 EXPRESSION AND SUPPRESS MAMMARY TUMOR METASTASIS

BACKGROUND

Breast cancer is the most common malignancy in women worldwide and the second leading cause of cancer mortality. Resection of the malignant tumor is still the standard primary treatment for breast cancer. Yet, metastasis of cancer to distant sites is the main cause of death.

Tumor cells are conditioned by their microenvironment at primary and secondary sites to promote growth and metastasis. It remains a challenge to prevent or suppress metastasis of tumor cells from their microenvironment into target tissues. The tumor microenvironment has been described as a tumor stroma or pre-metastatic/metastatic niche that promotes metastasis and therapy resistance.

Tumor-associated stromal cells produce tumor suppressor factors, such as nucleoside diphosphate kinase A, kangai 1, and interleukin 25 (IL-25), in the tumor microenvironment.

Tumor suppressor factors can restrict the development or metastasis of breast cancers. Significant efforts have been devoted to identifying molecular agents that promote expression of tumor suppressor factors, e.g., IL-25, thereby exhibiting therapeutic effects in suppressing tumor metastasis.

There is a need to develop a new method for suppressing mammary tumor metastasis via inducing a tumor suppressor factor.

SUMMARY

The present invention relates to use of benzofuran lignans for treating tumor metastasis. Unexpectedly, benzofuran lignans promote secretion of anti-cancer factors, e.g., IL-25, and effectively suppress tumor metastasis.

One aspect of this invention is a method of suppressing tumor metastasis, the method comprising administering to a subject in need thereof an amount of a compound of formula (I):

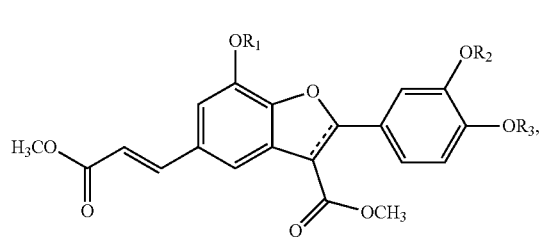

wherein each of $R_1$, $R_2$, and $R_3$, independently, is H, $C_{1-6}$ alkyl, or —C(O)$R_4$, $R_4$ being $C_{1-6}$ alkyl, $C_{3-8}$ cycloalkyl, $C_{2-8}$ heterocycloalkyl, $C_{6-14}$ aryl, or $C_{1-13}$ heteroaryl; and === is a single bond or a double bond, in which the amount is effective to induce secretion of an anti-cancer factor from tumor cells, the anti-cancer factor being IL-25, p53, Kangai 1, or nucleoside diphosphate kinase A.

The term "alkyl" herein refers to a straight or branched hydrocarbon group, containing 1-20 (e.g., 1-10 and 1-6) carbon atoms. Examples include methyl, ethyl, n-propyl, i-propyl, n-butyl, i-butyl, and t-butyl.

The term "cycloalkyl" refers to a saturated and partially unsaturated monocyclic, bicyclic, tricyclic, or tetracyclic hydrocarbon group having 3 to 12 carbons. Examples include cyclopropyl, cyclobutyl, cyclopentyl, cyclopentenyl, cyclohexyl, cyclohexenyl, cycloheptyl, and cyclooctyl.

The term "heterocycloalkyl" refers to a nonaromatic 5-8 membered monocyclic, 8-12 membered bicyclic, or 11-14 membered tricyclic ring system having one or more heteroatoms (e.g., O, N, P, and S). Examples include piperazinyl, imidazolidinyl, azepanyl, pyrrolidinyl, dihydrothiadiazolyl, dioxanyl, morpholinyl, tetrahydropuranyl, and tetrahydrofuranyl.

The term "aryl" refers to a 6-carbon monocyclic, 10-carbon bicyclic, 14-carbon tricyclic aromatic ring system, in which each ring may have 1 to 5 substituents. Examples of aryl groups include phenyl, naphthyl, and anthracenyl.

The term "heteroaryl" refers to an aromatic 5-8 membered monocyclic, 8-12 membered bicyclic, or 11-14 membered tricyclic ring system having one or more heteroatoms (e.g., O, N, P, and S). Examples include triazolyl, oxazolyl, thiadiazolyl, tetrazolyl, pyrazolyl, pyridyl, furyl, imidazolyl, benzimidazolyl, pyrimidinyl, thienyl, quinolinyl, indolyl, thiazolyl, and benzothiazolyl.

Alkyl, cycloalkyl, heterocycloalkyl, aryl, and heteroaryl mentioned herein include both substituted and unsubstituted moieties. Examples of substituents include, but are not limited to, halo, hydroxyl, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkyl, alkenyl, alkynyl, alkyloxy, aryl, heteroaryl, cycloalkyl, and heterocycloalkyl, in which alkyl, alkenyl, alkynyl, alkyloxy, aryl, heteroaryl cycloalkyl, and heterocycloalkyl may further be substituted.

Herein, the term "compound" refers to the compounds of Formula (I) described above, as well as their salts and solvates, if applicable. A salt can be formed between an anion and a positively charged group (e.g., amino) on a compound. Examples of a suitable anion include chloride, bromide, iodide, sulfate, nitrate, phosphate, citrate, methanesulfonate, trifluoroacetate, acetate, malate, tosylate, tartrate, fumarate, glutamate, glucuronate, lactate, glutarate, and maleate. A salt can also be formed between a cation and a negatively charged group. Examples of a suitable cation include sodium ion, potassium ion, magnesium ion, calcium ion, and an ammonium cation such as tetramethylammonium ion. A salt further includes those containing quaternary nitrogen atoms. A solvate refers to a complex formed between an active compound and a pharmaceutically acceptable solvent. Examples of a pharmaceutically acceptable solvent include water, ethanol, isopropanol, ethyl acetate, acetic acid, and ethanolamine.

Another aspect of this invention is a method of treating cancer, the method comprising administering to a subject in need thereof a first amount of a chemotherapy agent for inhibiting cancer growth and a second amount of a compound of formula (I), in which the first amount is effective to inhibit cancer growth and the second amount is effective to suppress cancer metastasis.

Also within the scope of this invention is a pharmaceutical composition for suppressing tumor metastasis, the pharmaceutical composition comprising a pharmaceutically acceptable carrier and a compound of formula (I).

Still within the scope of the present invention is a pharmaceutical composition for treating cancer, the pharmaceutical composition comprising a pharmaceutically acceptable carrier, a chemotherapy agent for inhibiting cancer growth, and a compound of formula (I).

This invention also covers use of such a composition described in the preceding paragraph for the manufacture of a medicament for treating cancer.

A composition for oral administration can be any orally acceptable dosage form including capsules, tablets, emulsions and aqueous suspensions, dispersions, and solutions.

In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. Oral solid dosage forms can be prepared by spray dried techniques; hot melt extrusion strategy, micronization, and nano milling technologies.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having an active compound can also be at administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active compound. Examples of other carriers include colloidal silicon oxide, magnesium stearate, cellulose, sodium lauryl sulfate, and D&C Yellow #10.

The above-described compounds or a pharmaceutical composition containing such a compound can be administered to a subject orally, parenterally, by inhalation spray, topically, rectally, nasally, buccally, or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

The term "treating" refers to application or administration of the compound to a subject with the purpose to cure, alleviate, relieve, alter, remedy, improve, or affect the disease, the symptom, or the predisposition. "An effective amount" refers to the amount of the compound which is required to confer the desired effect on the subject. Effective amounts vary, as recognized by those skilled in the art, depending on route of administration, excipient usage, and the possibility of co-usage with other therapeutic treatments such as use of other active agents.

The details of the invention are set forth in the description below. Other features, objects, and advantages of the invention will be apparent from the following drawings and detailed description of several embodiments, and also from the appending claims.

DETAILED DESCRIPTION

Figure 1A:
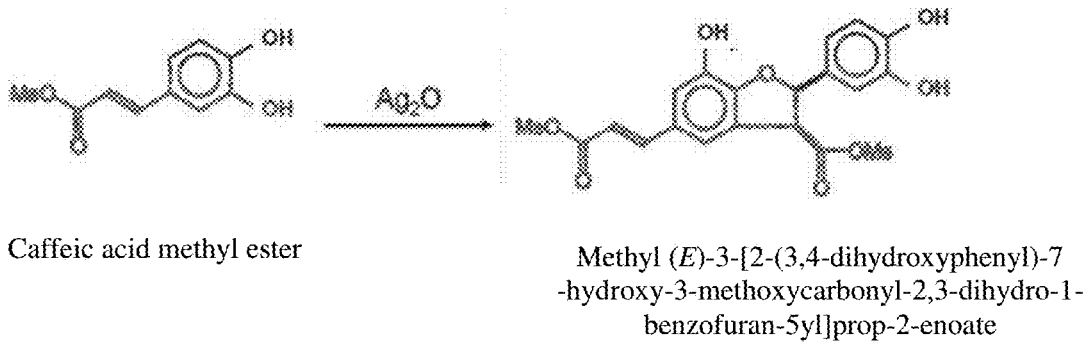
FIG. 1 is a schematic depiction of cytotoxic effects of dihydrobenzofuran lignan (Q2-3) on breast tumor cells.

Disclosed in detail herein is a method of using benzofuran lignans for suppressing tumor metastasis via inducing expression of anti-cancer factors, e.g., interleukin-25 (IL-25 or IL-17E).

Lignans are widespread natural products existing in plants. They have a variety of structures and exhibit a range of biological activities. A number of synthetic dihydrobenzofuran lignans are obtained by biomimetic oxidative dimerization of caffeic and/or ferulic acid methyl ester, followed by derivatization reactions. These synthetic lignans show potent antiangiogenic activity. Among them, methyl (E)-3-[2-(3,4-dihydroxyphenyl)-7-hydroxy-3-methoxycarbonyl-2,3-dihydro-1-benzofuran-5yl]-prop-2-enoate ("Q2-3") exhibits a significant anti-proliferation effect on various human cancer cell lines, including Jurkat, K562, and MCF-7 cells. It would be useful to investigate whether Q2-3 and other lignans could interfere with mammary tumor metastasis in mammary tumors.

It has been reported that IL-25 confers high anticancer activity, with little or no effect on nonmalignant cells. For example, see Furuta et al., Science translational medicine, 3, 78ra31 (2011). The apoptotic activity of IL-25 is mediated by differential expression of its receptor, IL-25R, which is expressed at high levels in tumors from patients with poor prognoses, but at low levels in nonmalignant breast tissues. This suggests that targeting the IL-25 signaling pathway may offer a novel therapeutic approach for advanced breast cancers. A method of this invention is directed to using benzofuran lignans for inducing IL-25 expression, thereby suppressing tumor metastasis.

The method includes administering to a subject in need thereof an amount of a compound of formula (I):

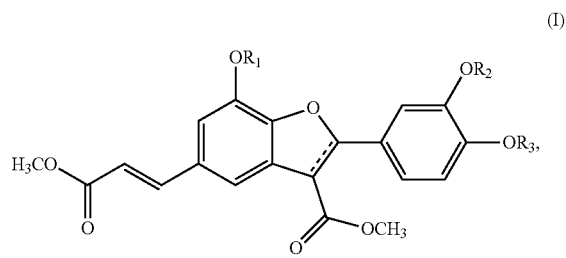

wherein each of $R_1$, $R_2$, and $R_3$, independently, is H, $C_{1-6}$ alkyl, or —C(O)$R_4$, $R_4$ being $C_{1-6}$ alkyl, $C_{3-8}$ cycloalkyl, $C_{2-8}$ heterocycloalkyl, $C_{6-14}$ aryl, or $C_{1-13}$ heteroaryl; and === is a single bond or a double bond, in which the amount is effective to induce secretion of an anti-cancer factor from tumor cells, the anti-cancer factor being IL-25, p53, Kangai 1, or nucleoside diphosphate kinase A.

The compound can be one of the following compounds:

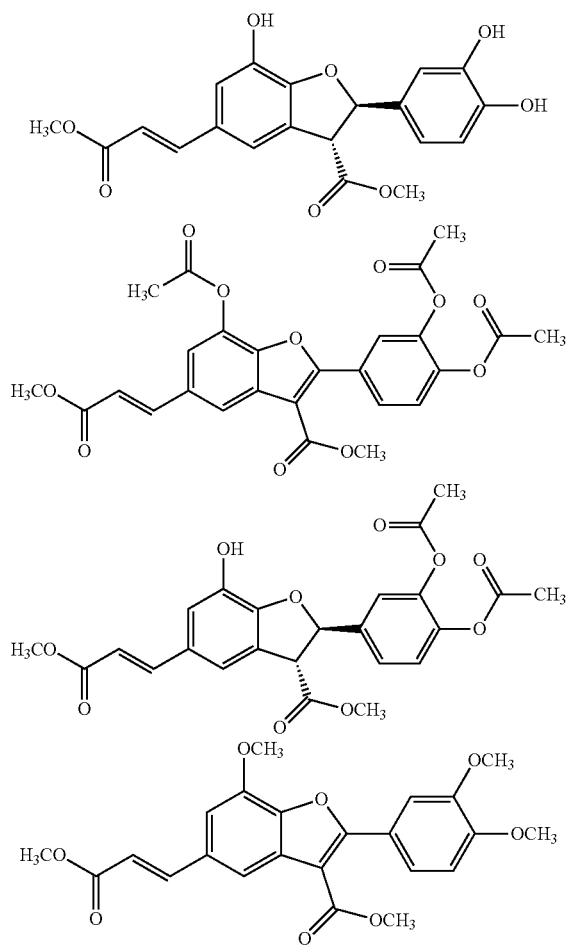

Also disclosed in detail herein is a method of treating cancer. The method includes administering to a subject in need thereof a first amount of a chemotherapy agent for inhibiting cancer growth and a second amount of a compound of formula (I) described above.

Examples of the cancer include, but are not limited to, breast cancer, non-small cell lung cancer, colorectal cancer, pancreatic cancer, ovarian cancer, skin cancer, prostate cancer, cancer of the brain or nervous system, head and neck cancer, testicular cancer, lung cancer, liver cancer, kidney cancer, bladder cancer, gastrointestinal cancer, bone cancer, cancer of the endocrine system, cancer of the lymphatic system, fibrosarcoma, neurectodermal tumor, mesothelioma, epidermoid carcinoma, and Kaposi's sarcoma.

The chemotherapy agent can be one of the following compounds: Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomyde; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Docetaxel Anhydrous; Doxorubicin; Doxorubicin Hydrochloride; Droloxifene; Droloxifene Citrate; Dromostanolone Propionate; Duazomycin; Edatrexate; Eflomithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Fluorocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfan3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Meiphalan; Menogaril; Mercaptopurine; Methotrexate; Methotrexate Sodium; Metoprine; Meturedepa; Mitindomide; Mitocarcin; Mitocromin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Pipolsulfan; Piroxantrone Hydrochloride; Plicamycin; Plomestane; Pommer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride, 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminol evulinic acid; amrubicin; amsacrine; anagrelide; anastrozole; andrographolide; angiogenesis inhibitors; antagonist D; antagonist G; antarelix; anti-dorsalizing morphogenetic protein-I; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin I; axinastatin 2; axinastatin 3; azasetron; azatoxin; aza osine; baccatin III derivatives; balanol; batimastat; BCR/ABL antagonists; benzochlorins; benzoylstaurosporine; beta-Iactam derivatives; beta-alethine; betaclamycin B; betulinic acid; bFGF inhibitor;

bicalutamide; bisantrene; bisaziridinylspermine; bisnafide; bistratene A; bizelesin; breflate; bropirimine; budotitane; buthionine sulfoximine; calcipotriol; calphostin C; camptothecinderivatives; canarypox IL-2; capecitabine; carboxamide-amino-triazole; carboxyamidotriazole; CaRest M3; CARN 700; cartilage derived inhibitor; carzelesin; casein kinase inhibitors (lCOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidenmin B; deslorelin; dexifosfamide; dexrazoxane; dexverapamil; diaziquone; didenmin B; didox; diethylnorspermine; dihydro-5-azacytidine; dihydrotaxol, 9-; dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-I receptor inhibitor; interferon agonists; interferons; interleukins; ioben-guane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatinA; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryllipidA+myobacterium cell wall sk; mopidamol; multiple drug resistance gene inhibitor; multiple tumor suppressor I-based therapy; mustard anti cancer compound; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone;

ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol;

phenazinomycin; phenylacetate; phosphatase inhibitors; picibanil; pilocarpine hydrochloride; pirarubicin; piritrexim; placetinA; placetin B; plasminogen activator inhibitor; platinum complex; platinum compounds; platinum-triamine complex; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron;

ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone BI; ruboxyl; safingol; saintopin; SarCNU; sarcophytolA; sargramostim; Sdi I mimetics; semustine; senescence derived inhibitor I; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin I; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer; antimetabolites; platinum-based agents; alkylating agents; tyrosine kinase inhibitors; anthracycline antibiotics; vinca alkaloids; proteasome inhibitors; macrolides; and topoisomerase inhibitors.

Further disclosed in detail is a pharmaceutical composition for suppressing tumor metastasis. The pharmaceutical composition contains a pharmaceutically acceptable carrier and a compound of formula (I).

This invention also covers a pharmaceutical composition for treating cancer. The pharmaceutical composition contains a pharmaceutically acceptable carrier, a chemotherapy agent for inhibiting cancer growth, and a compound of formula (I).

Methods for synthesizing compounds of formula (I) are well known in the art. See, for example, R. Larock, Comprehensive Organic Transformations ($2^{nd}$ Ed., VCH Publishers 1999); P. G. M. Wuts and T. W. Greene, Greene's Protective Groups in Organic Synthesis ($4^{th}$ Ed., John Wiley and Sons 2007); L. Fieser and M. Fieser, Fieser and Fieser's Reagents for Organic Synthesis (John Wiley and Sons 1994); L. Paquette, ed., Encyclopedia of Reagents for Organic Synthesis (2$^{nd}$ ed., John Wiley and Sons 2009); S. Miyazawa, M. Shinoda, T. Kawahara, N. Watanabe, H. Harada, D. Iida, H. Terauchi, J. Nagakawa, H. Fujisaki, A. Kubota, M. Ueda" Benzimidazole Compound" WO 2006112442; M. R. Mautino, S. Kumar, F. Jaipuri, J. Waldo, T. Kesharwani, M. N. Vahanian, C. J. Link, J. Lalonde, G. Prendergast, A. Muller, W. Malachowski "IDO Inhibitors" WO2009132238; T. Axenrod, J. Sun, K. K. Das, P. R. Dave, F. Forohar, M. Kaselj, N. J. Trivedi, R. D. Gilardi, J. L. Flippen-Anderson "Synthesis and Characterization of 5-Substituted 1,3-Diazacyclohexane Derivatives" *J. Org. Chem.* 2000, 65, 1200-1206; C. D. Magnusson, G. G. Haraldsson "Chemoenzymatic Synthesis of Symmetrically Structured Triacylglycerols Possessing Short-chain Fatty Acids" *Tetrahedron*, 2010, 66, 2728-2731.

The compounds of formula (I) thus prepared can be initially screened using a human mammary tumor cell growth inhibition assay for their efficacy in suppressing the growth of human mammary tumor cells, e.g., SKBR3 and MDA-MB-231 cells. They can be subsequently evaluated using in vivo assays, e.g., a mouse mammary tumor cell metastasis assay, for their efficacy in suppressing the metastasis of mouse mammary tumor cells after tumor resection. The selected compounds can be further tested to verify their efficacy in treating cancer. For example, a compound can be co-administered with a chemotherapy agent (e.g., docetaxel) to an animal (e.g., a mouse) having a tumor and its therapeutic effects are then assessed. Based on the results, an appropriate dosage range and administration route can be determined.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever. All publications cited herein are incorporated by reference.

Below are materials and methods used for preparing and testing the compounds of formula (I) described above.

Chemical Materials and Analysis

All chemicals and solvents were purchased from commercial suppliers and used as received. All reactions were carried out under an atmosphere of dry nitrogen. Reactions were monitored by TLC using Merck 60 F254 silica gel glass backed plates (5×10 cm); and zones were detected visually under ultraviolet irradiation (254 nm) or by spraying with phosphomolybdic acid reagent (Aldrich) followed by heating at 80° C. All flash column chromatography was performed with Merck Kieselgel 60, No. 9385, 230-400 mesh ASTM silica gel as the stationary phase. Proton ($^1$H) nuclear magnetic resonance spectra were measured on a Varian Mercury-300 or Varian Mercury-400 spectrometer. Chemical shifts were recorded in parts per million (ppm) on the delta (δ) scale relative to the resonance of the solvent peak. The following abbreviations were used to describe coupling: s=singlet; d=doublet; t=triplet; q=quartet; quin=quintet; br=broad; and m=multiplet.

Compounds

Methyl(E)-3-[2-(3,4-dihydroxyphenyl)-7-hydroxy-3-methoxycarbonyl-2,3-dihydro-1-benzo furan-5yl]prop-2-enoate, i.e., Q2-3, was prepared and characterized according to the method described in Pieters et al., Journal of medicinal chemistry, 42, 5475-5481 (1999). More specifically, methyl caffeate was dimerized using silver oxide in the presence of anhydrous benzene and anhydrous acetone and the product was purified by silica gel column chromatography with ethyl acetate n-hexane as the eluent. After evaporation, a colorless amorphous solid was obtained (18.8%). $^1$H NMR (CDCl$_3$, 400 MHz) δ ppm 3.64 (3H, s), 3.66 (3H, s), 4.14 (1H, d, J=7.2 Hz), 5.87 (1H, d, J=7.2 Hz), 6.12 (1H, d, J=16.0 Hz), 6.61 (1H, dd, J=8.4, 2.0 Hz), 6.69 (1H, d, J=8.4 Hz), 6.76 (1H, d, J=2.0 Hz), 6.90 (1H, br s), 6.93 (1H, br s), 7.43 (1H, d, J=16.0 Hz).

Other analogs were prepared in the manner as described above. For all biological tests, compounds were freshly dissolved in DMSO as a 50 mM stock solution and further dilutions were made in the same medium.

Cell Lines

4T1, TS/A, 3T3, SKBR3, WI38, NHDF, MCF-7, MCF-10A and MDA-MB-231 cells were obtained from American Type Culture Collection (Manassas, Va., USA). 4T1, 4T1-luc2 (i.e., 4T1 cells transfected with a IF4γ promoter-driven luciferase gene), MDA-MB-231, MDA-MB-231-luc2 (i.e., MDA-MB-231 cells transfected with a IF4γ promoter-driven luciferase gene), SKBR3, and WI38 cell lines were provided by Dr. Pei-Wen Hsiao (Academia Sinica, Taipei, Taiwan). The MCF-10A cell line was provided by Dr. Wen-Hwa Lee (Academia Sinica, Taipei, Taiwan). The NHDF cell line was provided by Dr. Been-Huang Chiang (Institute of Food Science and Technology, National Taiwan University, Taipei, Taiwan). The 4T1 and MDA-MB-231-luc2 cells were maintained in RPMI-1640 (Invitrogen, Carlsbad, Calif.) complete medium supplemented with 10% fetal bovine serum (FBS), 100 μM non-essential amino acids and 100 μM sodium pyruvate. The stably transfected 4T1-luc2 cells were maintained in RPMI complete medium supplemented with 0.5% puromycin. 3T3, NHDF, and TS/A cells were maintained in DMEM (Invitrogen, Carlsbad, Calif.) supplemented with 3.7 g/L sodium bicarbonate, 3.6 g/L HEPES and 10% FBS. MCF-7 cells were maintained in DMEM supplemented with 3.7 g/L sodium bicarbonate and 10% FBS. WI38 and M10 cells were maintained in MEM (Invitrogen, Carlsbad, Calif.) supplemented with 2.2 g/L sodium bicarbonate, 3.6 g/L HEPES, 1× non-essential amino acid, 1 mM sodium pyruvate and 10% FBS. SKBR3 and MDA-MB-231 cells were maintained in DMEM/F-12 (Invitrogen, Carlsbad, Calif.) supplemented with 2 g/L glucose and at 10% FBS. MCF-10A cells were maintained in DMEM/F-12 supplemented with 10 μg/ml insulin and 10% FBS. All culture media were supplemented with 100 μg/ml streptomycin, 100 unit/ml penicillin and 2 mM L-glutamine Cells were grown in a 5% CO$_2$ incubator at 37° C.

Construction of the 3-Dimensional Co-Culture System

To mimic the tumor microenvironment, a 3-dimensional (3-D) co-culture system was employed for the maintenance of mammary tumor cells and tumor-associated fibroblasts in adjacent collagen gels as reported in Rajan et al., *Nature protocols*, 1, 2753-2758 (2006). More specifically, rat tail collagen solution dissolved in acetic acid was neutralized by 1 N NaOH and then mixed with 10×PBS at 4° C. in a ratio of 9:1. To construct solid tumor-like cell mass, mouse (4T1 or TS/A cells) or human (MCF-7 or MDA-MB-231 cells) mammary tumor cells in each correspondent culture medium (1×10$^6$ cells/ml) were mixed with 4 mg/ml collagen solution in a ratio of 1:1. Four drops of collagen-tumor cell mixture (1×10$^4$ cells/10 μl/drop) were immediately and separately loaded on culture substratum in each well of a 6-well plate. The plates were then turned-over and kept in CO$_2$ incubator at 37° C. for collagen gelation. To prepare foundation collagen gel (FIG. 3c), culture media were mixed with 4 mg/ml collagen solution in a ratio of 1:1 (final concentration: 2 mg/ml). Aliquots of 1 ml foundation collagen solution were loaded on culture substratum and each was covered with collagen-tumor cell mixture. The culture plates were then kept in a $CO_2$ incubator at 37° C. for another 10 minutes. To prepare the fibroblast-containing collagen gel, mouse (3T3 cells) or human (WI38) fibroblasts in each corresponding culture medium ($3 \times 10^6$ cells/ml) were mixed with 4 mg/ml collagen solution in a ratio of 3:1. 1 ml fibroblast-containing collagen solution ($1 \times 10^6$ cells/1 ml/well), and were immediately loaded on each solid foundation collagen gel. Finally, culture media for each fibroblast type were added onto the top layer and were suspended with test compounds for different drug treatments. After 24 or 72 h co-culture of tumor cells and fibroblasts, liquid conditioned media were collected directly from each well for further tests.

For collection of total protein from fibroblasts in 3-D collagen gel, a layer of fibroblast-containing collagen gel was separated from foundation gel, by using a pipet tip to smoothly scrape the collagen layer. Each collected fibroblast-containing collagen gel was then minced in an eppendorf tube using scissors and dissolved in 1 ml Trizol (Invitrogen) or 1 ml Tissue Protein Extraction Reagent (Thermo), for extraction of total RNA and cellular protein, respectively.

MTT Assay

M10, WI38, SKBR3, and MDA-MB-231 cells ($1 \times 10^5$ cells/ml) dispensed in 96-well plates were incubated with vehicle or test compounds (Q2-3) for 24 h or 72 h in corresponding basal medium in a 5% CO2 incubator. To evaluate the effect of secreted IL-25 from Q2-3-treated fibroblasts on growth activity of mammary tumor cells, 4T1 and MDA-MB-231 cells ($1 \times 10^4$ cells/ml) dispensed in 96-well plates were incubated with control medium or different fibroblast conditioned media (200 µl/ml) which was changed daily for 5 days. All treatments were performed in triplicate cell cultures. The growth activity of cells was assayed using a 3-(4, 5-dimethythiazol-2-yl)-2, 5-diphenyl tetrazolium bromide (MTT; Sigma-Aldrich) colorimetric method. The absorbance at 570 nm (A570) was measured using a multiwall scanning spectrophotometer.

Mice

Female BALB/c mice and nude mice (BALB/cAnN.Cg-Foxnl$^{nu}$/CrlNarl) age 6-8 weeks were purchased from the National Laboratory Animal Breeding and Research Center, Taipei, Taiwan. Test mice were maintained in a laminar airflow cabinet kept at 24±2° C. and 40-70% humidity with 12-h light/12-h dark cycles under specific pathogen-free conditions. All manipulation and experimental protocols involving animals were approved by the Institutional Animal Care and Utilization Committee (IACUC) of Academia Sinica, Taipei.

4T1-Luc2 and MDA-MD-231-Luc2 Mammary Carcinoma-Tumor Resection Model

BALB/c mice were subcutaneously injected with 4T1-Luc2 cells ($5 \times 10^5$/100 µl PBS/mouse) into the fourth mammary fat pad under isoflurane anesthesia. Tumor growth was monitored by measuring the tumor volume according to the formula: volume=length×(width)$^2$/2. After tumors were established (180-200 mm$^3$) on day 14, test mice were divided into different groups (8 mice/group) and subjected to different treatments. At 15 days post tumor cell implantation, primary 4T1 tumors in situ were surgically removed by a tumor resection process. For drug treatment, mice were administered with different agents, including vehicle-control (PBS), mouse IL-25 protein (10 µg/kg, ProSpec, Vineland, N.J.), Q2-3 (2, 20 or 100 µg/kg) or docetaxel (2 mg/kg; Sigma-Aldrich), by intravenous injection for 3 weeks (3 injections/week) post tumor resection. For in vivo neutralization of mouse IL-25 activity, mice were treated intraperitoneally with either 100 µg anti-mouse IL-25 (IL-17E) antibody (clone 35B; Biolegend) or isotype control rat IgG (100 µg; rat, IgG1κ; Biolegend) at days 0, 3, 6, 9, 12, 15, 18 post tumor resection. To detect metastasis of human MDA-MD-231-Luc2 tumor cells, nude mice were injected subcutaneously with $5 \times 10^5$ MDA-MD-231-Luc2 cells into the mammary fat pad under isoflurane anesthesia. After tumors were established (250-350 mm$^3$) on day 24, test mice were divided into different groups (8 mice/group) and subjected to different treatments. At 25 days post tumor cell implantation, primary MDA-MD-231-Luc2 tumors in situ were surgically removed by a tumor resection process. For drug treatment, mice were administered with PBS (vehicle-control), Q2-3 (100 µg/kg), docetaxel (5 mg/kg) or Q2-3 (100 µg/kg)+docetaxel (5 mg/kg), by intravenous injection for 3 weeks (3 injections/week) post tumor resection. To monitor the progression of mouse (4T1) or human (MDA-MD-231) metastatic tumors, test mice treated with different drugs/agents were compared for their tumor metastatic activity and survival rate aftern another 8 weeks. Bioluminescence signals from the 4T1-luc2 tumor cells in test mice were analyzed using a non-invasive IVIS imaging system (Calipers, Hopkinton, Mass.) after intraperitoneal injection of 150 mg/kg D-luciferin (NanoLight technology, Pinetop, Ariz.).

Immunofluorescence Staining

Lung tissue specimens obtained from each tumor-resected mouse were fixed with 4% formalin and embedded in paraffin. For histological comparison, 6 µm-thick tissue sections were made and stained with hematoxylin and eosin (H&E). For immunofluorescence staining, fixed tissue sections were initially immersed in boiling sodium citrate buffer (0.01 M sodium citrate buffer, pH 6.0) for 30 min Lung tissue sections were blocked with 5% nonfat milk, and incubated with anti-FSP-1 antibody (1:200 dilution; Millipore), FITC-conjugated anti-CD206 antibody (1:200 dilution; Biolegend) or PE-conjugated anti-IL-25 antibody (1:100; R&D) in 1% nonfat milk for 1 hour at room temperature. Sections were then washed with PBS containing 0.1% Tween 20. To detect primary antibodies, some sections were incubated with FITC-conjugated anti-mouse-IgG (1:200; Jackson Immunoresearch, West Grove, Pa.) for FSP-1. 4',6-Diamidino-2-phenylindole dihydrochloride (1 µg/ml; Sigma-Aldrich) was used to stain the nuclei. Fluorescence microscopy evaluation of immunostained tissue sections was performed using a Zeiss Axiovert 200 M microscope (Carl Zeiss, Heidelberg, Germany) Images were captured with a digital camera (Orca ER, Hamamatsu) and processed using Axiovision 4.6.3 (Carl Zeiss).

Antibody-Mediated Depletion of IL-25 in Conditioned Medium

To pull down and deplete IL-25 protein molecules in 3T3 or MDA-MB-231 cell conditioned media, the Dynabeads antibody coupling kit (Life Technology; 14311D) was used according to the manufacturer's recommendations, yielding 10 mg/ml anti-IL25 antibody (ProteinTech, Chicago, Ill.)-coupled beads. The rabbit IgG (ProteinTech, Chicago, Ill.) was used as an isotype control antibody. After antibody coupling reaction, each conditioned medium (4 ml) was reacted with 2 mg antibody-coupled beads on a roller at RT for 1 h. The conditioned medium (CM) was then placed on a magnet for 1 min allowing the beads to be collected on the tube wall. The antibody-pulled down proteins from 3T3-CM, NHDF-CM or WI38-CM, were detected for the content of secreted IL-25 protein in each conditioned medium using western blot analysis. For some tests, the supernatants were collected and used for treating mouse or human mammary tumor cells.

IL-25R siRNA Treatment

MDA-MB231 and MCF-7 cells were seeded in 6-well plate at $10^5$ cells/well for 24 h before transfection. siRNAs used for knockdown of human IL-25 receptor (IL25-RB) were purchased from Biotools (Taiwan, ROC) as follows: IL-17RB-homo-448 (IL-25R-1 siRNA); IL-17RB-homo-519 (IL-25R-2 siRNA); IL-17RB-homo-956 (IL-25R-2 siRNA); negative control (Neg). At the beginning of transfection, each test IL25R siRNA oligomers (100 pmol) was diluted in 250 μl Opti-MEM I Reduced Serum Medium. Aliquots of 5 μl Lipofectamine 2000 transfection reagent (Invitrogen) were diluted with 250 μl Opti-MEM I Reduced Serum Medium. Diluted oligomers were mixed gently with the diluted Lipofectamine 2000 and incubated for 20 min at room temperature. The oligomer-Lipofectamine 2000 complexes were subsequently added to each well containing cells and medium. Cells were incubated at 37° C. for 72 h until test cells were ready to be treated with IL25 cytokine or a different CM.

Western Blot Assay

Cell lysates of 3T3, WI38, NHDF, MDA-MB-231, MCF-10A and MCF-7 or the IL-25-pulled down protein lysates from 3T3, WI38 or NHDF conditioned media were resolved by SDS PAGE using 8, 10 or 15% stepwise gels. The resolved proteins were transferred onto a PVDF membrane (Novex, San Diego, Calif.) and blotted with anti-IL-25, anti-IL-25R (rabbit polyclonal; ProteinTech, Chicago, Ill.), anti-Caspase-3 (rabbit plyoclonal; Abcam, Massachusetts, Mass.), anti-Caspase-8 (mouse monoclonal; Cell Signaling, Boston, Mass.), or anti-β-actin (rabbit polyclonal; Abcam). The membrane was blocked with 5% non-fat dry milk in PBST buffer [phosphate-buffered saline (PBS) containing 0.1% Tween 20] for 60 min at room temperature. Blotted membranes were then incubated overnight at 4° C. with specific, commercially available antibodies (1:1,000 dilutions). Loading of equal amounts of protein was assessed using the mouse β-actin protein as a reference. The blots were rinsed three times with PBST buffer for 5 min each. Washed blots were incubated with HRP-secondary antibody (goat polyclonal; 1:100,000 dilution; Abcam) and washed again three times with PBST buffer. The transferred proteins were visualized with an enhanced chemiluminescence (ECL) detection kit (Amersham Pharmacia Biotech, Buckinghamshire, UK). Quantification of protein in luminescent bands was performed using ImageJ software.

Flow Cytometry Assays

For detection of myeloid derived suppressor cells (MDSCs), cells from mouse lung tissue in each group were collected and stained for 30 min at 4° C. with antibodies against specific cell markers, including FITC-conjugated anti-mouse CD11b (for cell surface), APC-Cy7 conjugated anti-mouse Ly-6C and PE conjugated anti-mouse Ly-6G, (both for intracellular staining). All three antibodies were obtained from Biolegend, (San Diego, Calif.). The percentages of monocytic and granulocytic MDSCs were gated on $CD11b^+Ly-6C^+$ cells and $CD11b^+Ly-6G^+$ cells, respectively. For quantification of IL-25-expressing fibroblasts, individual cells isolated from mouse lung tissue were stained with Alexa Fluor® 647-conjugated anti-ER-TR7 (Novus, USA) and anti-FSP-1 (Millipore) primary antibody followed by FITC-conjugated secondary antibody (Abcam). PE-conjugated anti-mouse IL-17E antibody (R&D) was used for staining of intracellular IL-25 molecules in lung tissue. The percentage of IL-25-expressing fibroblasts was gated for $FSP-1^+ ER-TR7^+$ cells. Flow cytometry was performed on a FACS LSR II (BD, Netherlands) machine at the Agricultural Biotechnology Research Center (ABRC) in Academia Sinica.

Statistical Analysis

Statistical analysis was performed using an unpaired, two-tailed Student's t-test. Statistical analyses were conducted with GraphPad Prism 5.0 (GraphPad Software). Differences in tumor metastasis or mouse survival rate were determined by a log-rank (Mantel-Cox) test of the Kaplan-Meier curves. All statistical tests were two-sided. A P value of less than 0.05 was considered significant (*, P<0.05; , P<0.01; *, P<0.001; n.s, not significant).

Example 1: Cytotoxic Effects of Q2-3 on Mammary Carcinoma and Non-Malignant Cells A study was performed to evaluate the cytotoxic effects of Q2-3 on mammary carcinoma and non-malignant cells.

FIG. 1 is a schematic depiction of cytotoxic effects of dihydrobenzofuran lignan (Q2-3) on breast tumor cells. (a): Scheme for synthesis of Q2-3 (methyl (E)-3-[2-(3,4-dihydroxyphenyl)-7-hydroxy-3-methoxycarbonyl-2,3-dihydro-1-benzofuran-5yl]prop-2-enoate) from two caffeic acid methyl ester molecules. (b) and (c): MTT assays for cytotoxic effect of Q2-3 on SKBR3 ($ER^-Her^+$ human breast cancer cell line), MDA-MB-231 ($ER^-Her^-$ human breast cancer cell line), M10 (human normal epithelial cell line) and WI38 (human lung fibroblast cell line). $2 \times 10^4$ cells were seeded and compared for their growth activity after treatment with Q2-3 for 24 or 72 h. The beginning cytotoxic dosage of Q2-3 was detected at 0.3 μM, with >50% kill rate on SKBR3 and MDA-MB-231 cells.

Methyl (E)-3-[2-(3,4-dihydroxyphenyl)-7-hydroxy-3-methoxycarbonyl-2,3-dihydro-1-benzofuran-5yl]prop-2-enoate, i.e., Q2-3, was synthesized from caffeic acid methyl ester following the scheme shown in FIG. 1a. Q2-3 was approximately 96% pure as a single isomer.

Figure 1B:
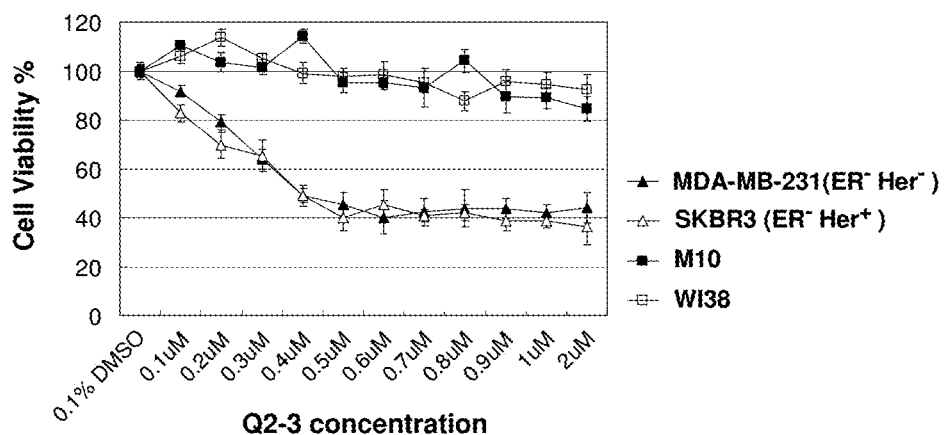
Figure 1C:
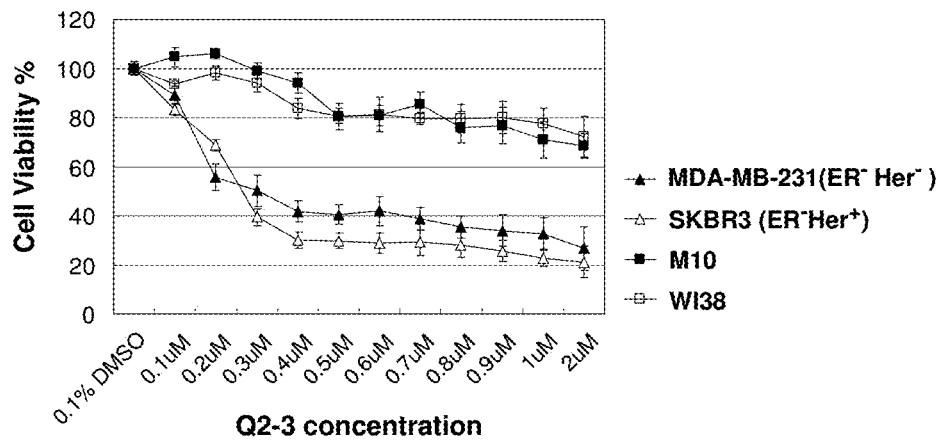

The effects of Q2-3 on cell viability were tested on four different cell lines, i.e., normal human mammary epithelial (M10), normal human mammary fibroblast (WI38), and two human mammary tumor cells (SKBR3 and MDA-MB-231), by treating cells with Q2-3 at various concentrations for 24 h (FIG. 1b) and 72 h (FIG. 1c). Both FIGS. 1b and 1c show that, as compared to cells in the control group (0.1% DMSO), Q2-3 effectively suppressed the growth (≥60% inhibition) of SKBR3 and MDA-MB-231 cells at a relatively low concentration (≥0.5 μM). By contrast, M10 and WI38 cell lines showed much higher resistance to treatment with Q2-3, exhibiting ≥80% viability at 2 μM.

These results indicate that Q2-3 exhibited high cytotoxicity effects on mammary tumor cells, but not on normal human mammary epithelial cells and fibroblasts.

Example 2: Effects of Q2-3 on Suppressing Metastasis of 4T1 Mammary Tumor Cells in Mice A study was performed to evaluate the effects of Q2-3 on suppressing metastasis of 4T1 mammary tumor cells in mice.

FIG. 2 is a schematic depiction of effects of Q2-3 on suppressing metastasis of 4T1 mammary tumor cells in mice, after a tumor resection process. (a): Representative bioluminescent images of tumor-bearing mice (n=8 per group) after in vivo treatment with PBS (0.1% DMSO in saline), doxorubicin (2 mg/kg), or Q2-3 at different dosages, after resection of the orthotopic primary tumors. In the PBS-treated group (vehicle), three mice died before 3 weeks post tumor resection. The red signal represents the highest level on the colorimetric scale. (b): Quantification of tumor metastasis by measuring luciferase activity in p/s/cm$^2$/sr in mice revealed along the indicated time course (n=8 per group). (c): Survival of test mice after different treatments. P<0.05, were obtained between the control (DMSO) and Q2-3-treated (20 or 100 μg/kg) groups (Kaplan-Meier results were analyzed by log-rank test). (d): Effect of Q2-3 (2, 20, or 100 μg/kg) on the population change of monocytic (CD11b$^+$Ly6C$^+$) and granulocytic (CD11b$^+$Ly6G$^+$) MDSCs in lung tissues of test mice were quantified by flow cytometry analysis, using the FACS system and DIVA software.

Figure 2A:
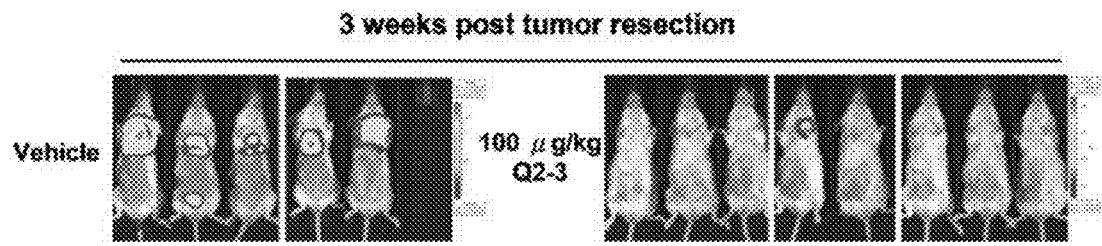
FIG. 2 is a schematic depiction of effects of Q2-3 on suppressing metastasis of 4T1 mammary tumor cells in mice, after a tumor resection process.
Figure 2B:
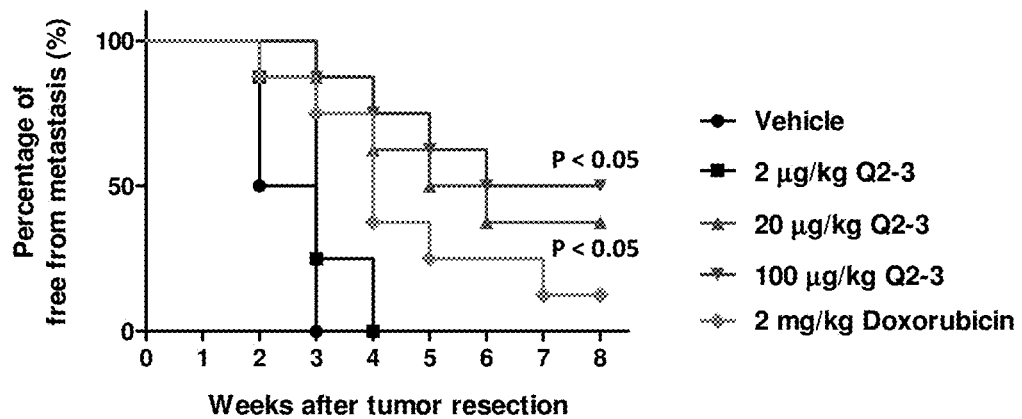
Figure 2C:
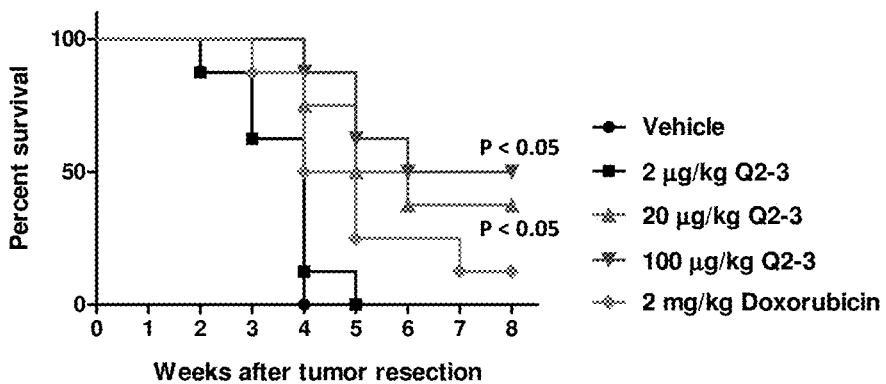

To investigate the anti-metastatic effects of Q2-3, transgenic luciferase-expressing mouse 4T1-Luc2 cells were injected into the mammary fat pad of test mice. At 15 days post tumor cell implantation, in situ 4T1 tumors were carefully removed by a surgical resection process. As shown in FIG. 2, tumor metastatic activity and survival time of control and Q2-3-treated mice were examined and compared over the following 8 weeks. FIG. 2a shows that, by detecting the luminescent activity of 4T1-Luc2 cells as an indication of tumor metastasis, Q2-3 treatment (≥20 μg/kg) was found to significantly suppress the metastasis of 4T1 cells to the lung. FIG. 2b shows that treatment with Q2-3 at a relatively low dosage (≥20 μg/kg) had much higher anti-metastatic activity than treatment with doxorubicin (2 mg/kg), a clinical drug used for treating human breast cancers. Finally, FIG. 2c shows that Q2-3 treatment also significantly increased the survival rate of tumor-resected mice.

These results show that in vivo administration of Q2-3 effectively prevented mammary tumor metastasis after a tumor resection process.

The importance of myeloid derived suppressor cells (MDSCs) in regulation of tumor growth has been well documented. For example, see Gabrilovich et al., *Nature reviews Immunology*, 12, 253-268 (2012). A drastic accumulation and activation of MDSCs is also recognized as an important pathologic feature of tumor progression and this can be readily observed in the 4T1 tumor resection model, with which the populations of both monocytic and granulocytic MDSCs in metastatic tissues could be detected at high abundance at 3-4 weeks post tumor resection.

Figure 2D:
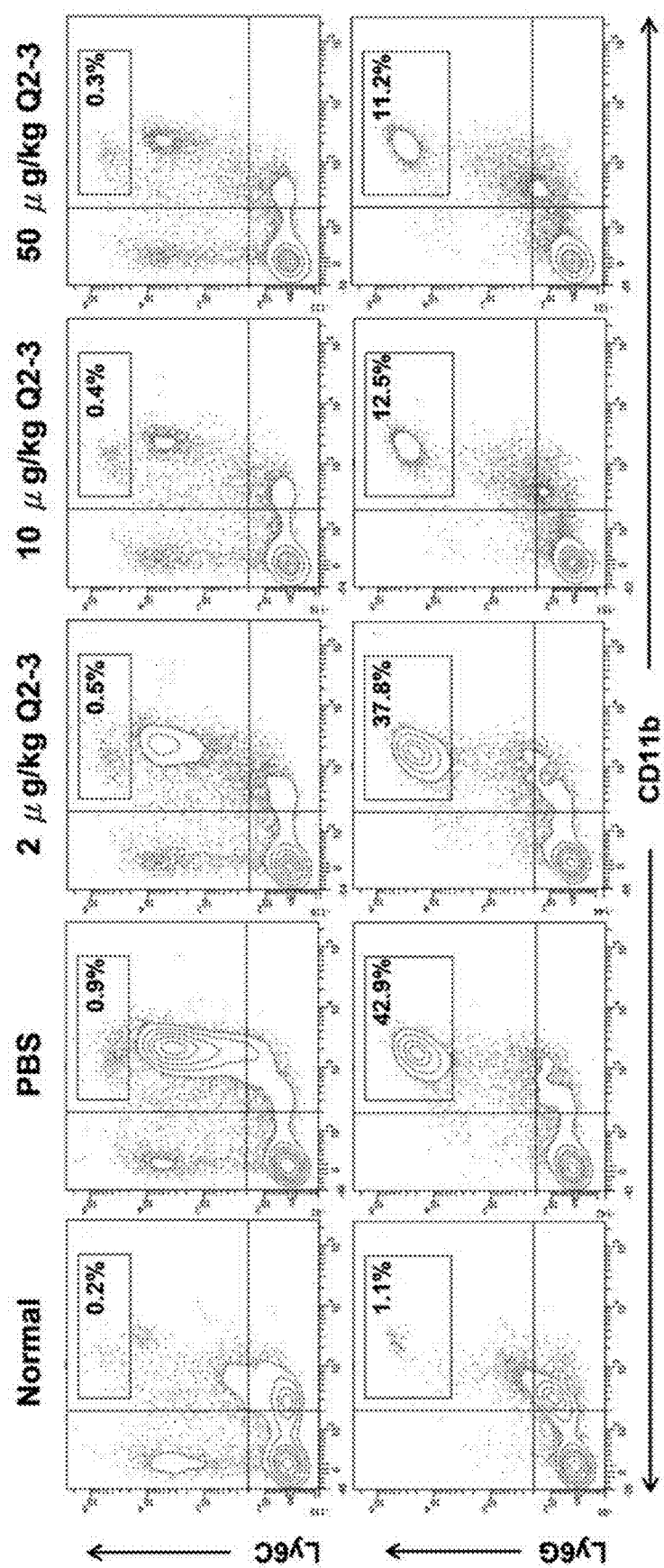

Suppressive effects of Q2-3 on in vivo expansion of MDSC populations were also evaluated for both the monocytic (CD11b$^+$Ly6C$^+$) and granulocytic (CD11b$^+$Ly6G$^+$) subsets of MDSCs. The populations of these two MDSC cell types in lung tissues of test mice were analyzed and compared at 3 weeks post tumor resection. FIG. 2d shows that, as compared to the PBS (vehicle control)-treated mice, both CD11b$^+$Ly6C$^+$ and CD11b$^+$Ly6G$^+$ MDSC populations in Q2-3-treated (10 μg/kg) mice were significantly decreased from 0.9% to 0.4% and from 42.9% to 12.5%, respectively.

These results indicate that Q2-3 exhibited anti-metastatic effects on mammary tumor cells in vivo.

Example 3: Effects of Q2-3 on Upregulating IL-25 Expression in Lung Fibroblasts Both In Vivo and In Vitro A study was performed to evaluate the effects of Q2-3 on upregulating IL-25 expression in lung fibroblasts, under both in vivo and in vitro conditions.

FIG. 3 is a schematic depiction of effects of Q2-3 on upregulating IL-25 expression in lung fibroblasts both in vivo and in vitro. (a): IF staining. Lung tissues of control (0.1% DMSO in PBS), Q2-3-treated and docetaxel-treated mice were collected at 21 days post tumor resection and stained for the presence of IL-25-expressing cells (red and indicated with arrowheads), FSP-1 (green) and DAPI (blue). T stands for tumor and A stands for alveoli. (b): Effect of Q2-3 on population change of FSP-1$^+$ER-TR7$^+$ cells and their IL-25 expression level in lungs of test mice, quantified using flow cytometry. The percentage of IL-25$^+$ fibroblasts in gated FSP-1$^+$ER-TR7$^+$ cells was further analyzed using the FACS system and DIVA software. FSP-1, fibroblast specific protein-1; ER-TR7, Erasmus University Rotterdam-thymic reticulum-7. (c): Construction of 3-D cell co-culture system for mammary tumor cells and tumor-associated fibroblasts. (d): Western blot analyses of the expression of mouse IL-25 in 3T3 fibroblasts. (e): Western blot analyses of the expression of human IL-25 in WI38 fibroblasts, in response to Q2-3 treatments in 3-D culture. Some fibroblasts in the upper layer were co-cultured with mammary tumor cells as indicated. The expression level of IL-25 in 3T3 and WI38 fibroblasts were quantified and normalized using ImageJ software. Fold-changes of IL-25 expression level in test samples were normalized with the value in fibroblasts of the 0 h group and were indicated by the number labeled in blue. β-Actin served as an internal control.

Figure 3A:
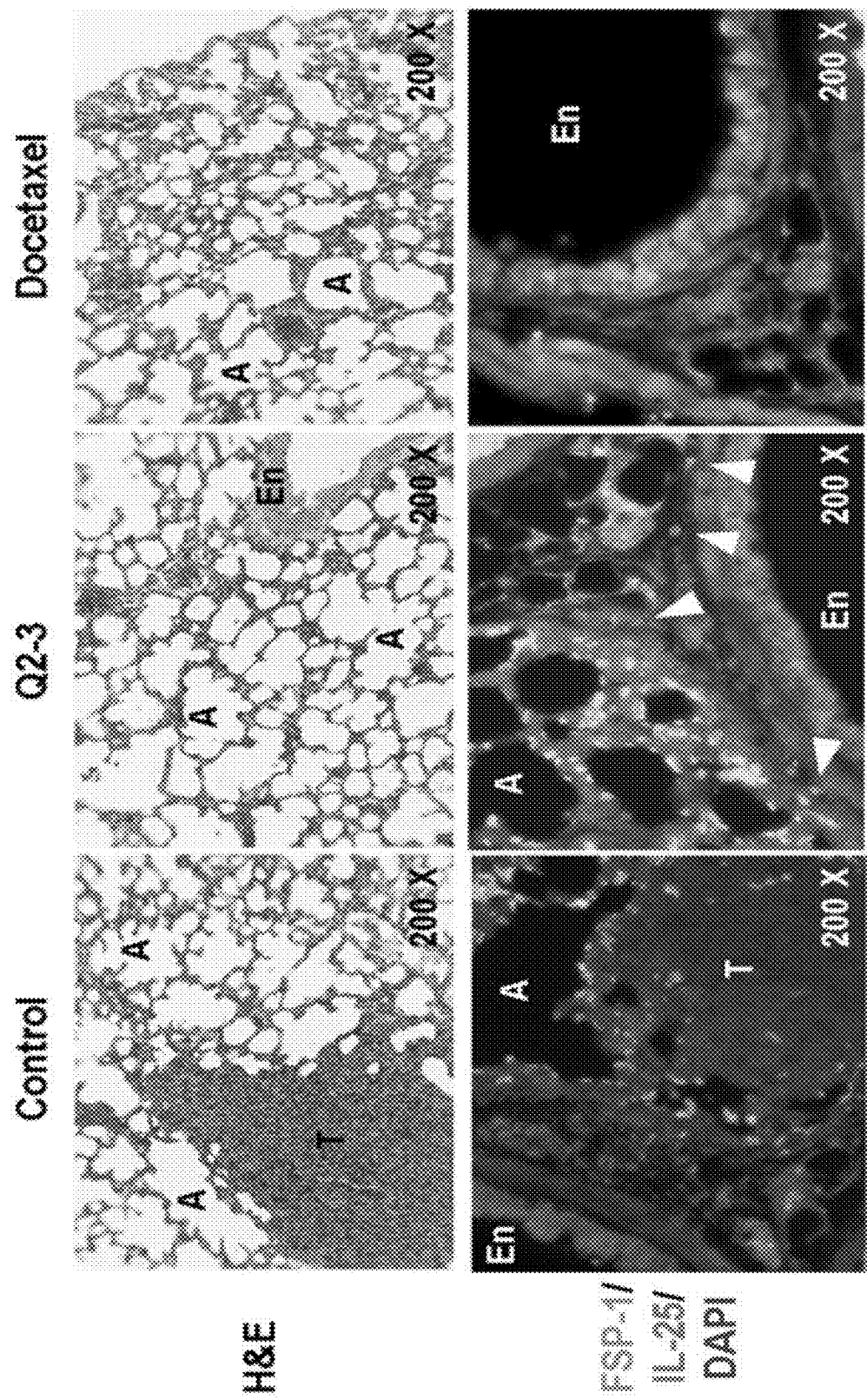
FIG. 3 is a schematic depiction of effects of Q2-3 on upregulating IL-25 expression in lung fibroblasts both in vivo and in vitro.

In view of the potent anti-metastatic effect of Q2-3 described in EXAMPLE 2, it can be hypothesized that in vivo administration of Q2-3 could confer a regulatory effect on the target metastatic tissues. To characterize the physiological significance of the modulatory activity of Q2-3, analysis was conducted to evaluate the expression of several secreted cytokines in vivo in the lung tissue of test mice. The change in the expression level of IL-25 upon Q2-3 treatment was particularly striking. As shown in FIG. 3a, administration of Q2-3 (100 μg/kg) conferred a readily detectable stimulatory effect on IL-25 activity in lung fibroblasts, which were found to mainly surround the main pulmonary artery and vein tissue. In lung tissues of control and DT-treated mice, little or no IL-25 expression was detected in lung fibroblasts.

This result suggests that Q2-3-induced IL-25 expression in the fibroblasts of the lung tissue microenvironment, which is not a pharmacological target of conventionally used anti-cancer drugs.

Figure 3B:
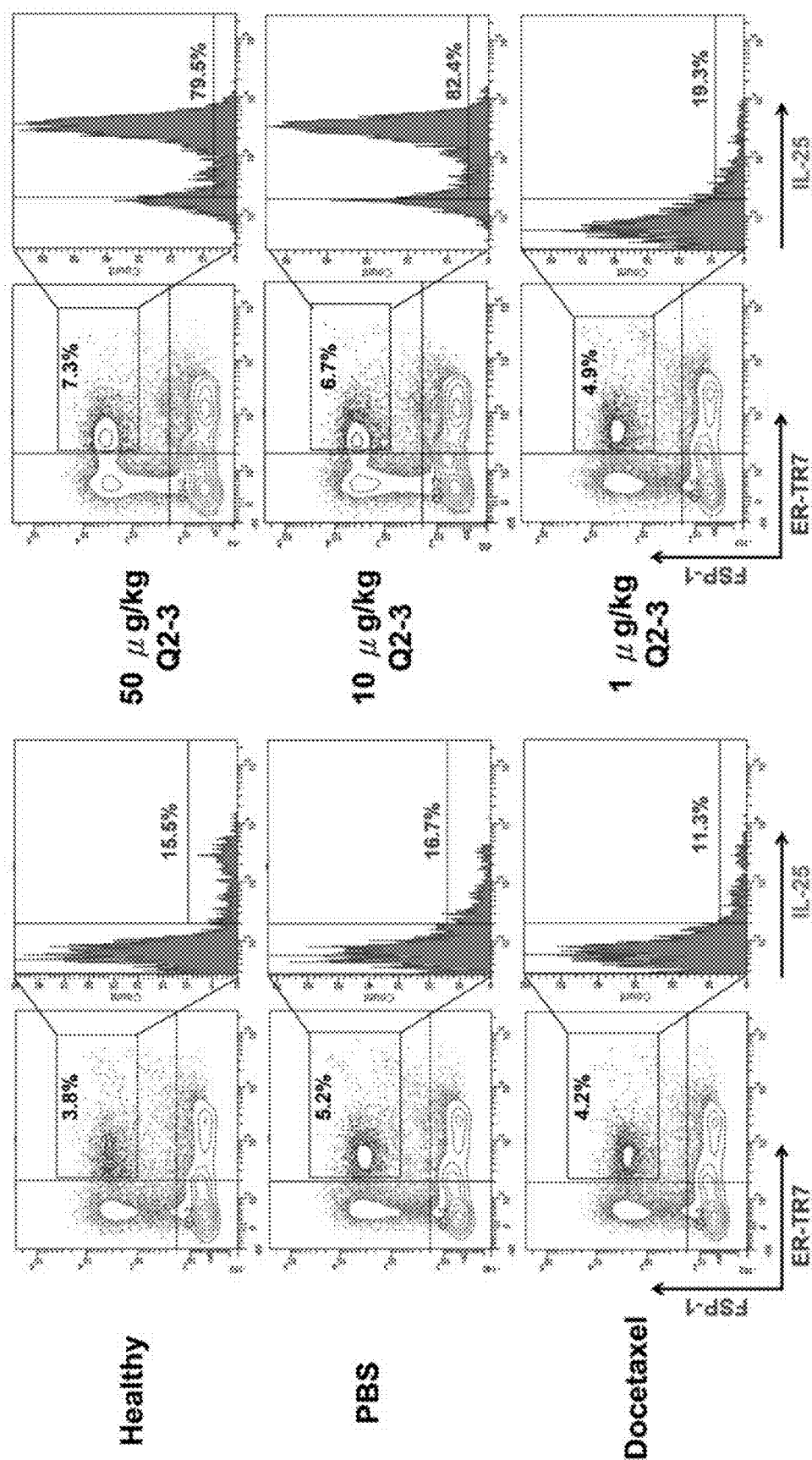
Figure 3C:
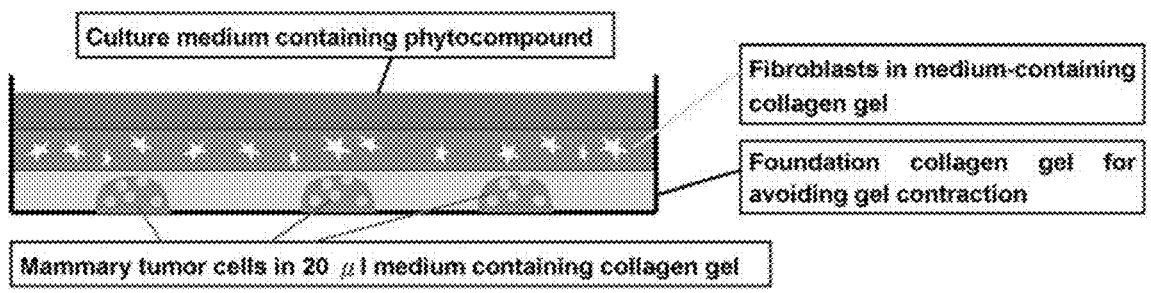

To quantify the change in cell population of IL-25-expressing lung fibroblasts in response to Q2-3 treatment, populations of FSP-1$^+$ER-TR7$^+$ cells in test mouse lung tissues were quantified and compared for their IL-25 expression level at 3 weeks post tumor resection. FIG. 3b shows that, compared with the PBS (vehicle control)-treated mice, the cell population of IL-25$^+$ fibroblasts (FSP-1$^+$ER-TR7$^+$ IL-25$^+$ cells) in Q2-3-treated mice was found to be drastically increased from 16.7% to 79.5%. In addition, the total FSP-1$^+$ER-TR7$^+$ fibroblast population in Q2-3-treated mice was also detected to be increased from 5.2% to 7.3%, in a dose dependent manner By contrast, treatment with DT, a drug tested in parallel as a reference, did not increase the quantity and the IL-25 expression level of FSP-1$^+$ER-TR7$^+$ cells in lungs of test mice. Interestingly, the increase in the FSP-1$^+$IL-25$^+$ fibroblast population induced by Q2-3 seen in the lung was not detected in spleen or other tissues tested (data not shown), suggesting that the expression of endogenous IL-25 in pulmonary fibroblasts is tissue-specific, and inducible by drug treatment.

This result is consistent with the data shown in FIG. 3a, and further quantifies and supports the finding that Q2-3 stimulated pulmonary fibroblasts in vivo.

Figure 3D:
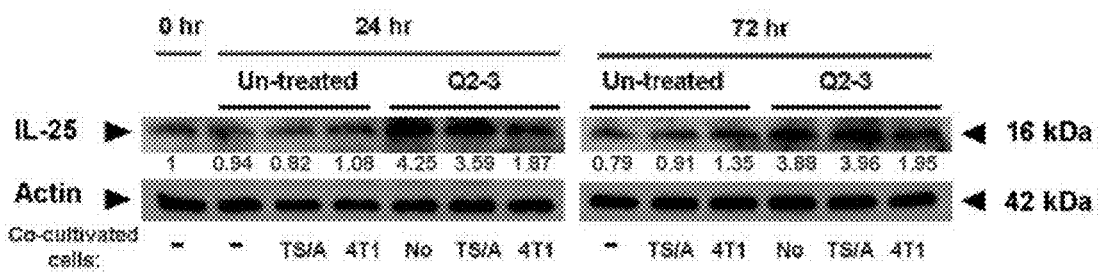
Figure 3E:
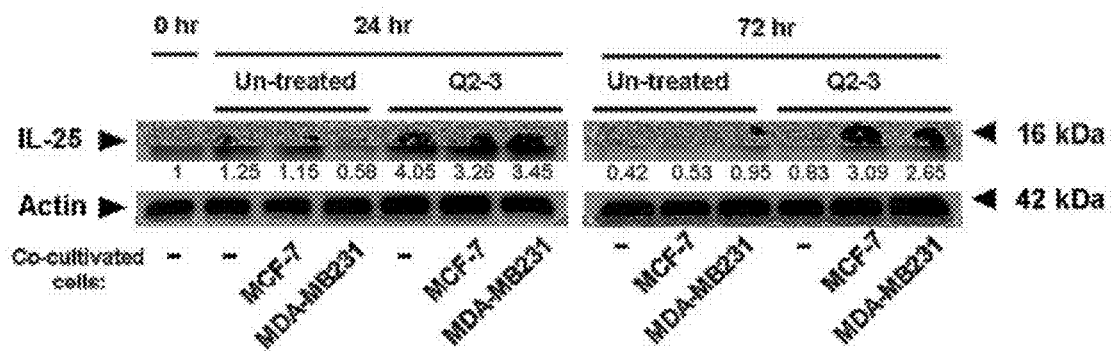

To further study the specific effect of Q2-3 on fibroblasts in the tumor microenvironment, a three-dimensional (3-D)

cell co-culture system was employed to mimic the in vivo mammary tumor microenvironment. See FIG. 3c. In this system, high density of mouse or human mammary carcinoma cells were mixed in medium-containing collagen ($1\times10^5$ cells/20 µl medium-containing collagen solution) and dropped onto the culture substratum (4 colonies/well). $1\times10^6$ mouse (3T3 cells) or human (NHDF and WI38 cells) fibroblasts were grown in the upper layer of 3-D collagen gel and co-cultured with or without test mammary tumor cells in the lower layer. With this artificial reconstruction approach, the expression levels of IL-25 in mouse and human fibroblasts were compared, alone or in co-cultivation with test mammary tumor cells. In addition, this 3-D setup was also used to study the effect of Q2-3, which was supplemented into the test culture media. It was observed that expression of IL-25 in both mouse (3T3) and human (WI38) fibroblasts were increased after Q2-3 treatment for 24 h or 72 h, as shown in FIGS. 3d and 3e.

This result suggests that Q2-3 significantly upregulated IL-25 expression in both mouse and human fibroblasts.

Example 4: Effects of IL-25 Secreted by Q2-3 Treatment on Suppressing the Growth of Mouse and Human Metastatic Mammary Tumor Cells A study was performed to evaluate the effects of IL-25 secreted by Q2-3 treatment on suppressing the growth of mouse and human metastatic mammary tumor cells.

FIG. 4 is a schematic depiction of effects of IL-25 secreted by Q2-3 treatment on suppressing the growth of mouse and human metastatic mammary tumor cells. (a): Western blot analysis of the IL-25 secretion activity of mouse (3T3) and human (WI38) fibroblasts in response to Q2-3 treatment. Different fibroblast-conditioned media (CM), including 3T3-CM and WI38-CM, were collected from the 3-D cultures and were stained with coomassie blue, revealing that the total protein level in tested CM was normalized. Aliquots of 3T3-CM and WI38-CM were immuno-depleted for IL-25. Rabbit IgG (isotype control antibody) was used as a negative control in this immunodepletion test. Amounts of IL-25 (relative staining intensity) were further normalized with the value detected for Q2-3-treated 3T3-CM (blue) or Q2-3-treated WI38-CM samples (purple). (b): Reduction in cytotoxicity of 3T3-CM on 4T1 cells after immunodepletion of IL-25. The control (fresh) medium, 3T3-CM, Q2-3-treated 3T3-CM, Q2-3-treated 3T3-CM with added IL-25 protein, Q2-3-treated 3T3-CM with the immuno-depletion of IL-25, and Q2-3-treated 3T3-CM with control IgG-mediated immunodepletion, were compared for their suppressive effect on growth of 4T1 cells. (c): Reduction in cytotoxicity of WI38-CM on MDA-MB-231 after immunodepletion of IL-25. Similarly, WI38-CM with added IL-25 protein, WI38-CM with the immuno-depletion of IL-25, or Q2-3-treated WI38-CM with control IgG-mediated immunodepletion, were compared for their suppressive effect on growth of MDA-MB-231 cells. The growth activity of 4T1 cells or MDA-MB-231 cells was determined using MTT assay at 5 days post cultivation, and was normalized to the number of viable cells in the control group (with fresh medium only). Error bars, ±SD. n=3. *, $P<0.05$, , $P<0.01$, *, $P<0.005$ (two-tailed Student's t-test). (d): Western blot analysis of IL-17RA and IL-17RB (IL-25R) expression in mammary cancer cell line (MDA-MB-231 and MCF-10A). Knock down of human IL-25R (both 56 and 33 kDa molecules) expression in MDA-MB-231 cells was also performed with three designed siRNAi treatments. The negative control (Neg) RNAi was used as a nonspecific control. (e): Western blot analysis of the cleavage of caspases 8 and 3 in MDA-MB-231 cells. MDA-MB-231 cells were treated by control-, Neg RNAi- or IL-25R RNAi, for 48 h. Some cells in each test group then were treated with recombinant human IL-25 (200 ng/ml), WI38-CM, or WI38-CM with the immunodepletion of IL-25, for another 24 h. β-Actin served as an internal control. Similar results were obtained from three independent experiments. White arrowheads, cleaved protein. Black arrowheads; uncleaved protein.

To characterize and analyze the possible suppressive effect of fibroblast-secreted IL-25 on growth activity of mammary tumor cells, the levels of secreted IL-25 protein in conditioned media of test mouse and human fibroblasts were collected and compared by using an anti-IL-25 antibody-mediated immunoprecipitation approach. Prior to immuno-precipitation, aliquot samples of conditioned medium from Q2-3-treated fibroblasts, including 3T3 fibroblast-conditioned media (3T3-CM) and WI38 fibroblast-conditioned media (WI38-CM), were immuno-depleted for IL-25. In this study, anti-rabbit IgG antibody (isotype control) was used as a negative control for immuno-depletion. The quantity of IL-25 in each conditioned medium and the efficiency of immuno-depletion for IL-25 were then assessed by immunobloting analysis.

Figure 4A:
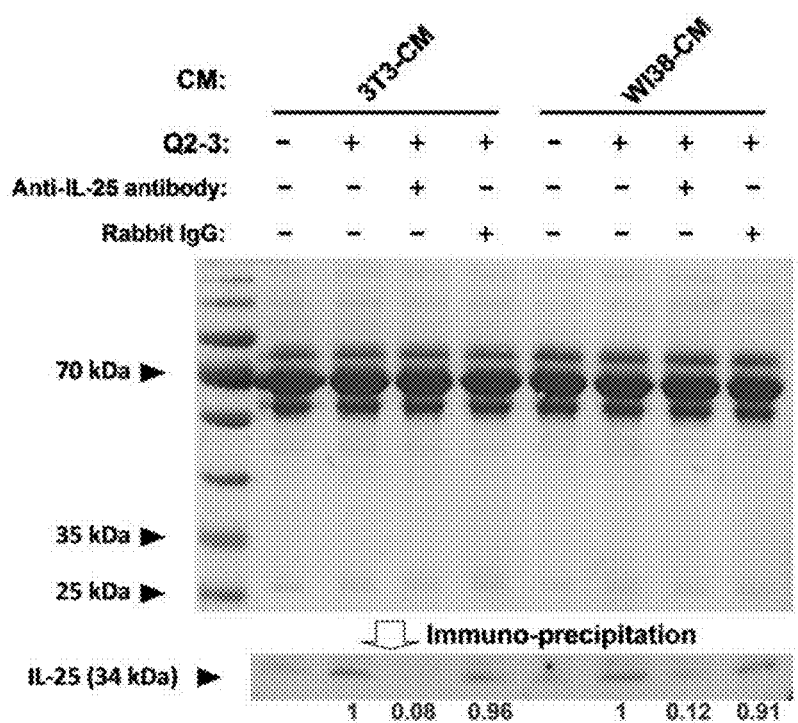
FIG. 4 is a schematic depiction of effects of IL-25 secreted by Q2-3 treatment on suppressing the growth of mouse and human metastatic mammary tumor cells.
Figure 4B:
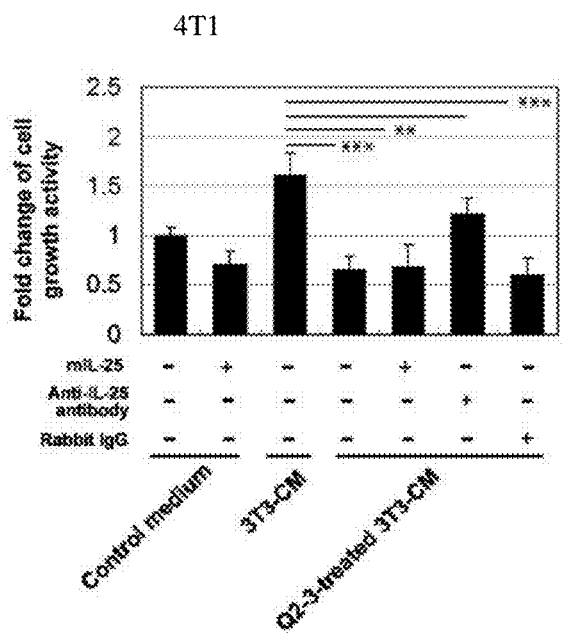

FIG. 4a shows that the levels of secreted IL-25 in the Q2-3-treated fibroblast-conditioned media were found to be significantly higher than that in the untreated fibroblast-conditioned media. Importantly, it also demonstrates that most secreted IL-25 (90%) in both human and mouse Q2-3-treated fibroblast-conditioned media could be immuno-depleted by using anti-IL-25 antibody. Only a very small fraction (4 to 9% decrease) of nonspecific protein binding was detected for the isotype control antibody, showing high specificity and efficiency of the used anti-IL-25 antibody.

Figure 4C:
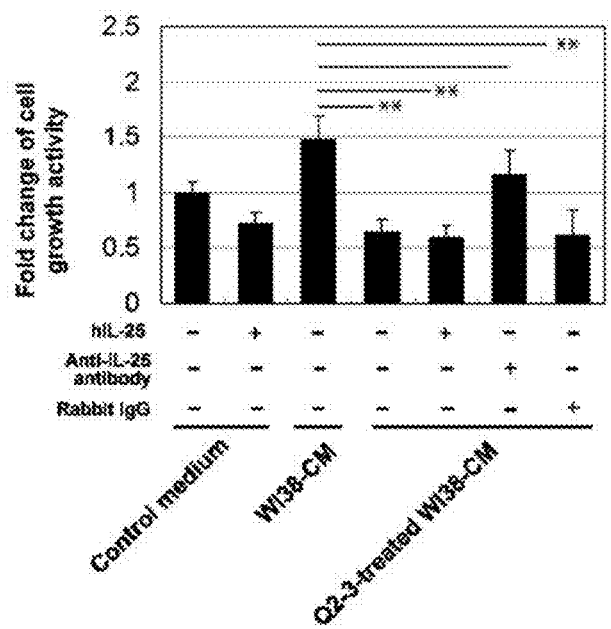

The conditioned media immuno-depleted for IL-25 from cultivation of mouse and human fibroblasts was employed to culture 4T1 and MDA-MB-231 tumor cells, respectively. In this study, fresh conditioned media were applied every 24 hours for 5 days. 4T1 cells cultured with 3T3-CM showed much higher growth activity than cells cultured with fresh medium only. See FIG. 4b. This result is consistent with that obtained from MDA-MB-231 cells as shown in FIG. 4c.

These results suggest that fibroblasts could release important cellular and molecular factors for tumor cell expansion. In addition, exogenously added IL-25 protein (100 ng/ml for human and mouse IL-25 recombinant protein) decreased the growth activity of test 4T1 and MDA-MB-231 cells. In agreement, 4T1 cells cultured with Q2-3-treated 3T3-CM (FIG. 4b) or MDA-MB-231 cells cultured with Q2-3-treated WI38-CM (FIG. 4c) also showed relatively decreased cell growth activity, as compared with IL-25 protein-treated tumor cells. By contrast, depletion of IL-25 attenuated the growth-suppressive effect of Q2-3-treated fibroblasts CM on mouse (FIG. 4b) and human (FIG. 4c) mammary tumor cells. This attenuation was not observed by the use of isotype IgG antibody.

These results indicate that IL-25 secreted from fibroblasts by Q2-3-treatment plays a critical role in suppressing the growth activity of metastatic mammary tumor cells.

Figure 4D:
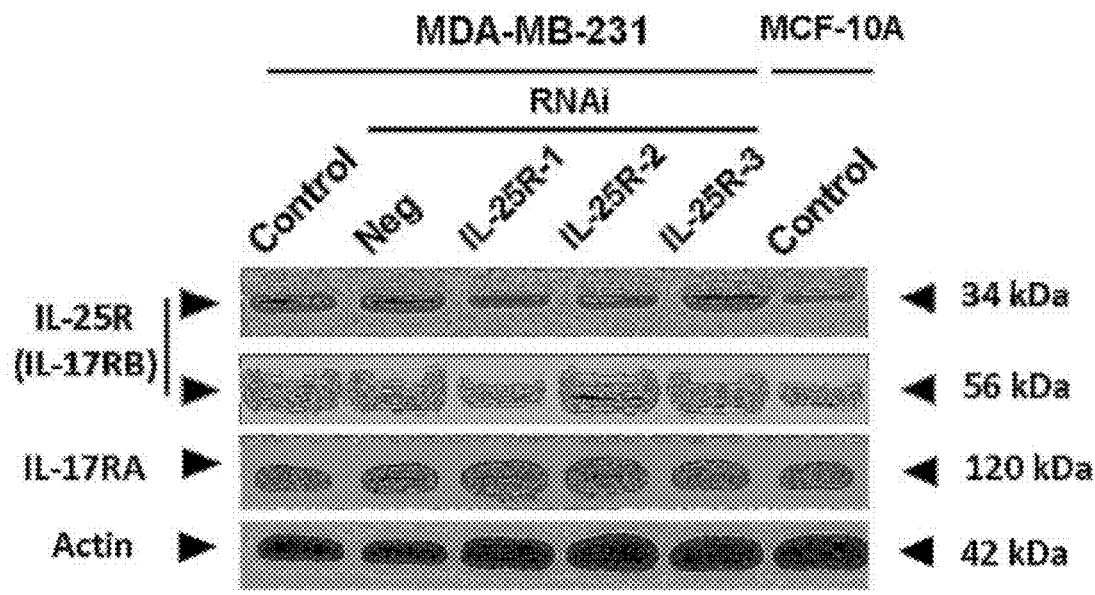

To examine whether the growth-suppression activity of fibroblast-secreted IL-25 protein was mediated by IL-25R (IL17RB) signaling in mammary tumor cells, the expression of IL-25R was knocked down in metastatic mammary carcinoma cells (MDA-MB-231 cells) using IL-25R-specific siRNA. To test the knockdown efficiency of three designed IL-25R siRNAs, the IL-25R expression was screened in MDA-MB-231 cells (as shown in FIG. 4d) and compared with that in MCF-10A cells, a nonmalignant and ER-negative breast cancer cell line with low levels of expression of IL-25R. The negative control siRNA (non-targeting siRNA) treatment did not have a significant effect on expression of IL-25R. Among the three tested siRNAs, treatment with IL-25R-1 siRNA exhibited the highest knockdown efficiency for the expression of both IL17RB isoforms (33 and 56 kDa) in treated MDA-MB-231 cells. In addition, none of the IL-25RB siRNA treatments resulted in a detectable change in the expression level of IL-17RA, another component of the IL-25R heterodimer. As such, the IL-25R-1 siRNA preparation was therefore chosen for subsequent experiments.

Figure 4E:
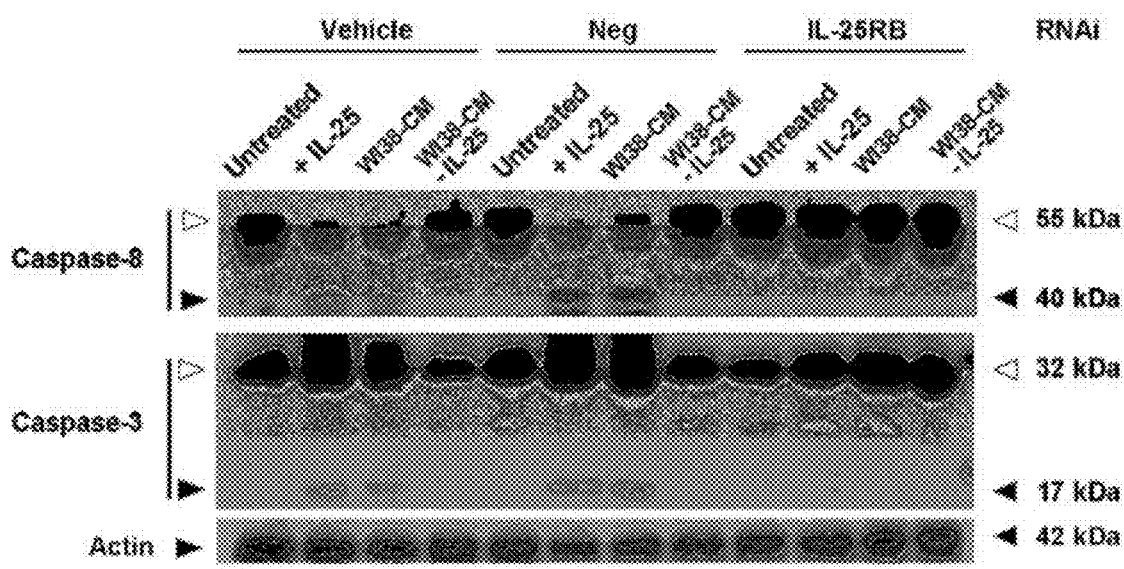

FIG. 4e shows that treatment with IL-25 (100 ng/ml) or Q2-3-treated WI38 conditioned medium (Q2-3-WI38-CM) resulted in the cleavage of caspases 8 and 3 in MDA-MB-231 cells, indicating the activation of apoptosis. Consistent with the result in FIG. 4C, depletion of IL-25 from Q2-3-WI38-CM also rescued test tumor cells from caspase cleavage. By contrast, in MDA-MB-231 cells treated with IL-25R siRNA, treatment with IL-25 or Q2-3-WI38-CM was not able to induce the cleavage activity of caspases 8 and 3.

These results suggest that the IL-25 secreted by Q2-3-treated WI38 fibroblasts effectively induced IL25R-mediated cell apoptosis, causing the death of breast cancer cells.

Example 5: Roles of IL-25 Expression in the Anti-Metastatic Activity of Q2-3 on Mammary Tumor Cells A study was performed to evaluate the roles of IL-25 expression in the anti-metastatic activity of Q2-3 on mammary tumor cells.

FIG. 5 is a schematic depiction of roles of IL-25 expression in the anti-metastatic activity of Q2-3 on mammary tumor cells. (a): Representative bioluminescent images of tumor-resected mice (n=8 per group) after in vivo treatment with PBS (0.1% DMSO in saline), Q2-3 (100 μg/kg; 3 injections/week), anti-mouse IL-25 Ab (100 μg/mice; 2 injections/week), Q2-3+IL-25 Ab, or Q2-3+isotype IgG, at 3 weeks post tumor resection. The label "D" in the photograph denotes the mice died before 3 weeks post tumor resection. (b): Quantification of tumor metastasis by measuring luciferase activity (p/s/cm$^2$/sr) in mice, as revealed along the indicated time course (12 weeks). (c): Survival of test mice after different treatments. n.s, no significant difference between the "Q2-3" and "Q2-3+Anti-IgG" groups. **, significance of $P<0.01$, was obtained between the "Q2-3" and "Q2-3+Anti-IL-25" groups (Kaplan-Meier results were analyzed by log-rank test).

To address whether IL-25 expression plays a key role in the anti-metastatic activity of Q2-3 on mammary tumor cells, an antibody-neutralization approach was employed to deplete the in vivo IL-25 activity in the same 4T1 tumor resection model described in EXAMPLE 2. Again by detecting the luminescent activity derived from transgenic 4T1-Luc2 cells in test mice, co-treatment of mice with Q2-3 (100 μg/kg) and anti-mouse IL-25 antibody (100 μg/injection/mice), unlike the anti-metastatic effect detected for the "Q2-3 treatment only" group, resulted in full metastasis activity as observed for the control (PBS) group.

By contrast, when using an irrelevant anti-IgG antibody preparation for this antibody depletion test, the Q2-3 effect on anti-metastasis was virtually sustained. See FIGS. 5a and 5b.

These results show that IL-25 clearly played a central role in anti-metastatic activity of Q2-3.

Figure 5A:
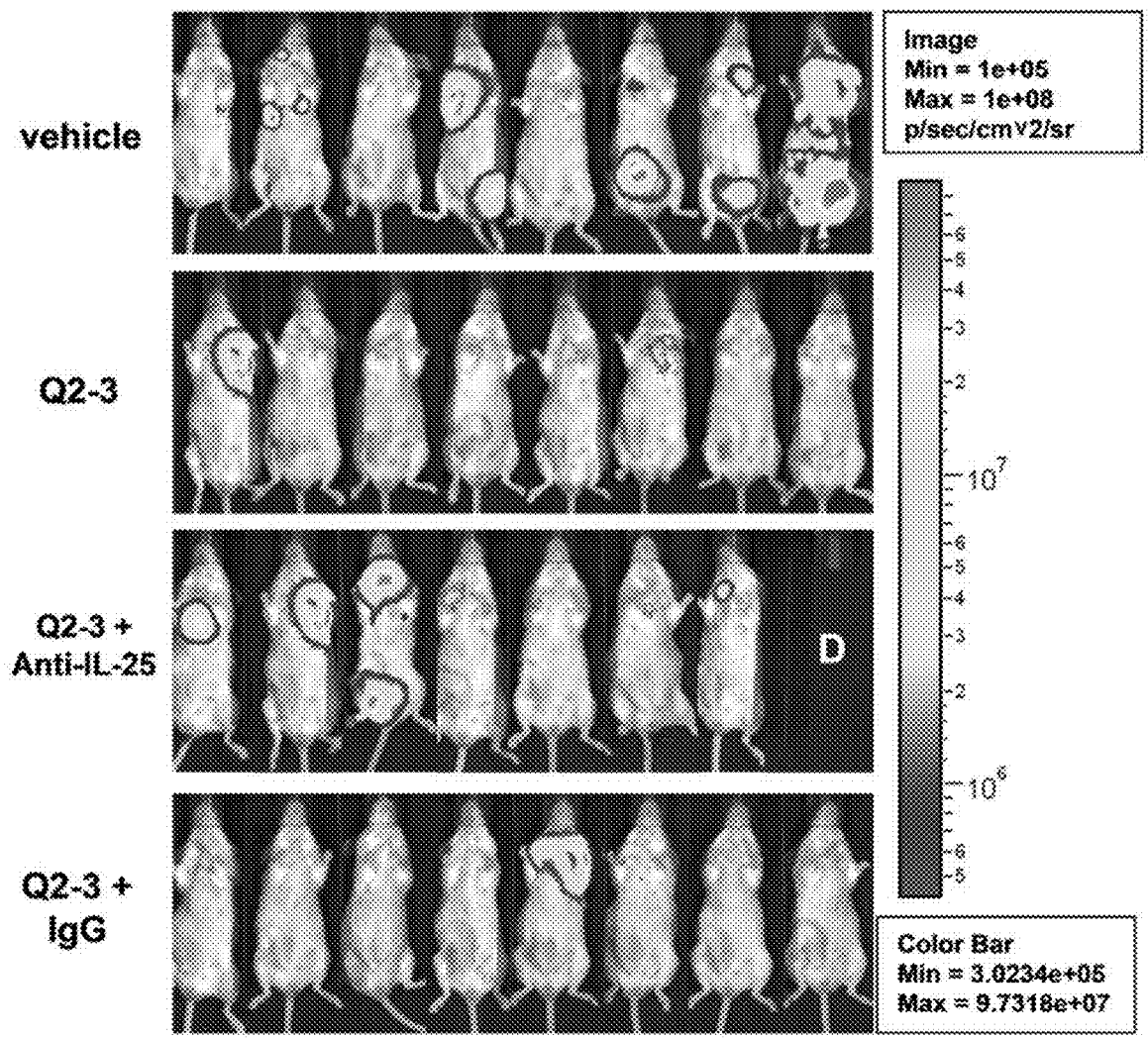
FIG. 5 is a schematic depiction of roles of IL-25 expression in the anti-metastatic activity of Q2-3 on mammary tumor cells.
Figure 5B:
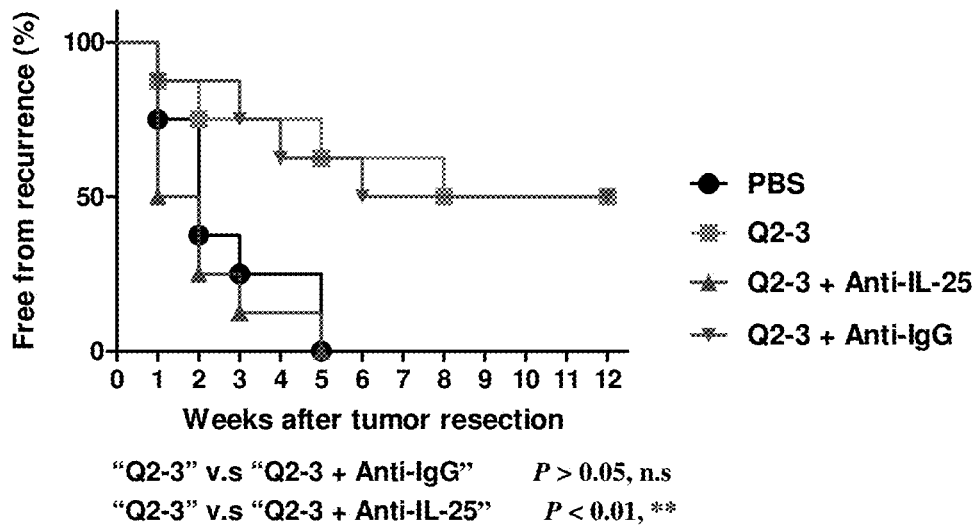
Figure 5C:
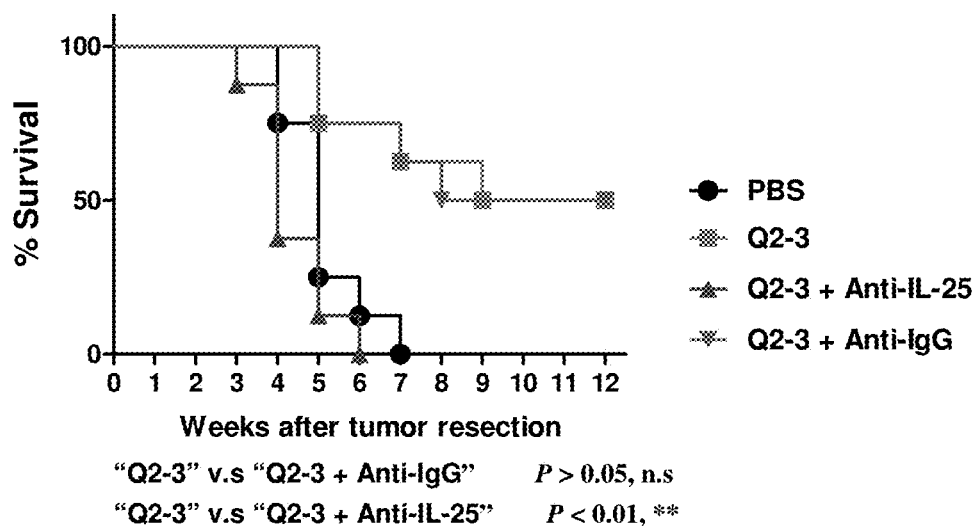

FIG. 5c shows that the mice in the co-treatment group (Q2-3+Anti-IL-25) also exhibited a survival rate that was decreased to a similar level to that of the control (PBS) group, as compared to the mice of the Q2-3-treated group. Interestingly, even in vivo administration of anti-mouse IL-25 antibody was repeatedly found to detectably promote 4T1 metastasis, as compared to that of the control tumor-resected mice, as seen in FIGS. 5a and 5b.

This result suggests that the presence or expression of endogenous IL-25 caused weak suppression of tumor metastasis in the untreated, tumor-resected mice. In other words, the in vivo anti-metastatic effect of Q2-3 was mediated by endogenous IL-25 activity.

Example 6: Evaluation of the Anti-Metastatic Activity of Co-Treatment with Q2-3 and IL-25

A study was performed to evaluate the anti-metastatic activity of co-treatment of mice with Q2-3 and IL-25.

Figure 6A:
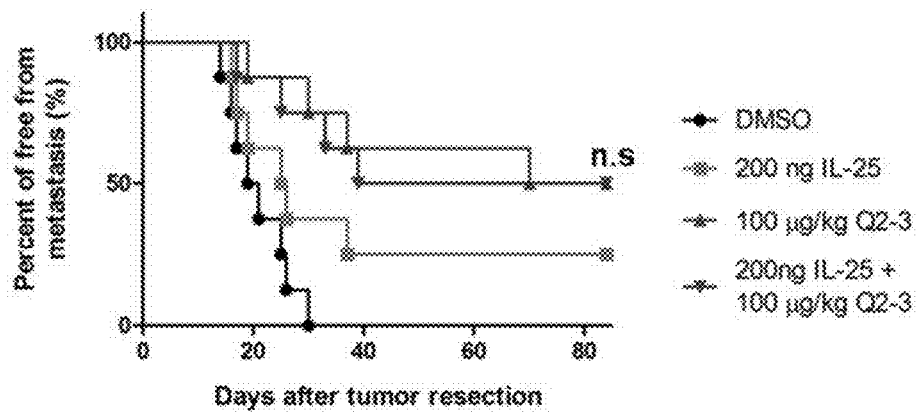
FIG. 6 is a schematic depiction of evaluation of the anti-metastatic activity of co-treatment with Q2-3 and IL-25.
Figure 6B:
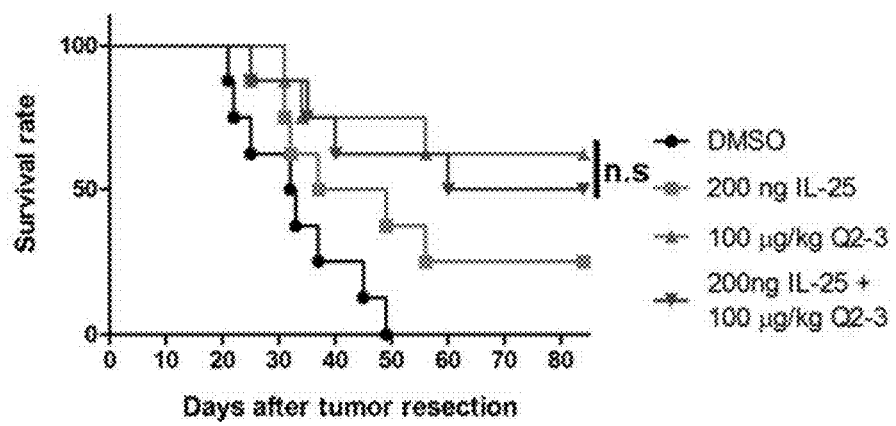

FIG. 6 is a schematic depiction of evaluation of the anti-metastatic activity of co-treatment with Q2-3 and IL-25. (a): Tumor-resected mice (n=8 per group) were treated with PBS (0.1% DMSO in saline), IL-25 (200 ng/mice), Q2-3 (100 μg/kg), or co-treated with IL-25 and Q2-3 for 3 weeks. Quantification of tumor metastasis by measuring luciferase activity in p/s/cm$^2$/sr in mice revealed along the indicated time course. (b): Survival of test mice after different treatments. n.s, no significant difference between the Q2-3 and co-treatment groups (Kaplan-Meier results were analysed by log-rank test).

IL-25 treatment in vivo was studied for its additive effect versus overlapping effect. The co-treatment of mice with Q2-3 (100 μg/kg) and IL-25 (10 μg/kg) was found to confer a similar, rather than additive effect on anti-metastatic activity, as detected in a Q2-3 treatment only mouse group. See FIG. 6a. Consistently, the mice in the co-treatment group also showed a survival rate increased to a level similar to that in the Q2-3-treated group, as compared to the mice in the untreated group. See FIG. 6b. In other words, the anti-metastatic effect of Q2-3 in vivo could be effectively substituted by the administration of exogenous IL-25. These results further support the critical role of IL-25 in the anti-metastatic effect of Q2-3.

Example 7: Evaluation of the Anti-Metastatic Activity of Co-Treatment with Q2-3 and Docetaxel A study was performed to evaluate the anti-metastatic activity of co-treatment of mice with Q2-3 and docetaxel (DT).

Figure 7A:
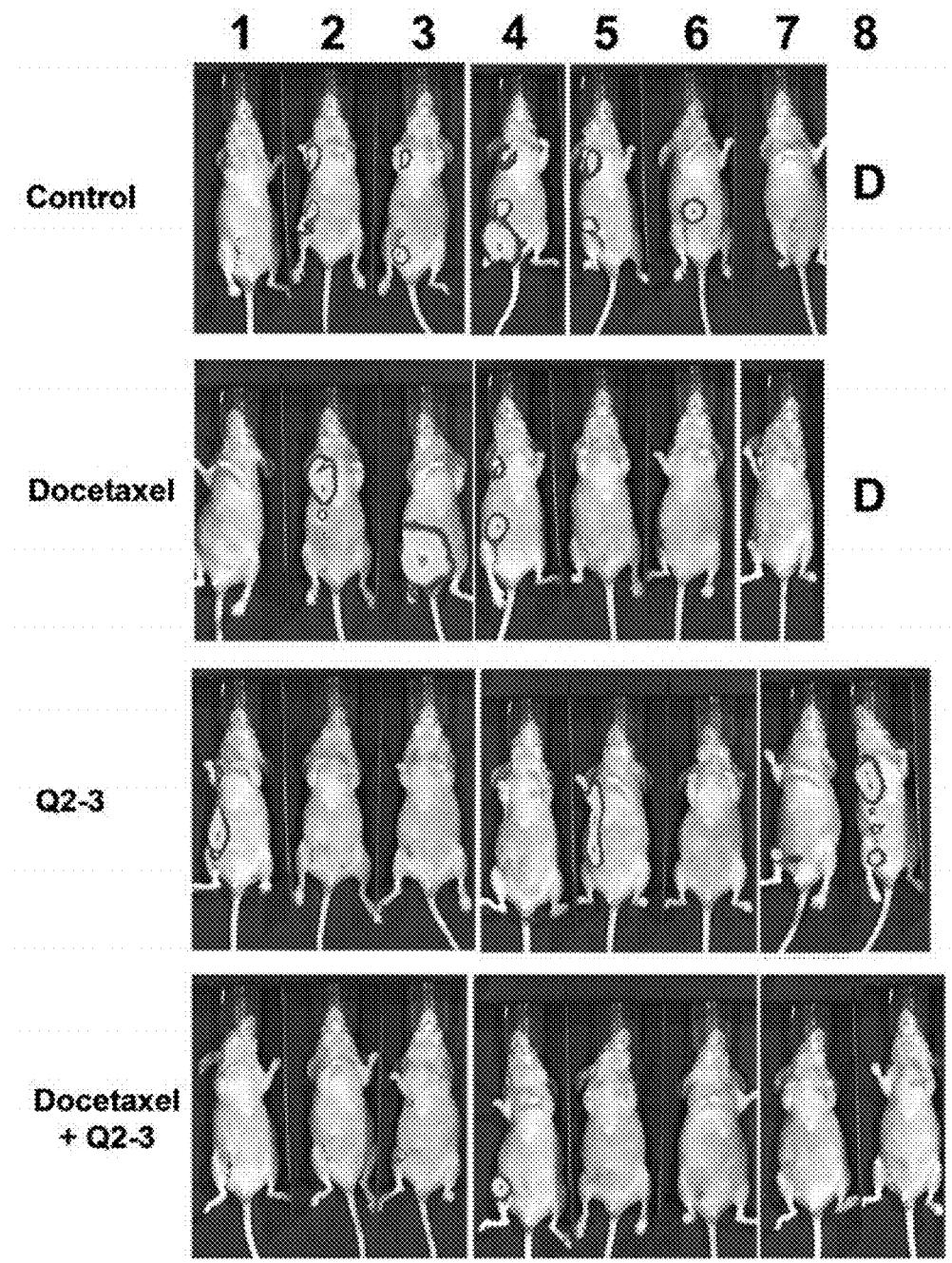
FIG. 7 is a schematic depiction of evaluation of the anti-metastatic activity of co-treatment with Q2-3 and docetaxel.

FIG. 7 is a schematic depiction of evaluation of the anti-metastatic activity of co-treatment with Q2-3 and docetaxel. (a): Representative bioluminescent images of MDA-MB-231 tumor-bearing nude mice (n=8 per group) after in vivo treatment with PBS (0.1% DMSO in saline), Q2-3 (100 μg/kg), docetaxel (5 mg/kg), or co-treatment with docetaxel and Q2-3 for 3 weeks, after resection of the orthotopic primary tumors. In PBS-treated (control) and docetaxel-treated groups, one mice was died before 3 weeks post tumor resection. (b): Quantification of tumor metastasis by measuring luciferase activity in p/s/cm$^2$/sr in mice revealed along the indicated time course. (c): Survival of test mice after different treatments. $P<0.05$, were obtained between the docetaxel- and co-treated mice (Kaplan-Meier results were analysed by log-rank test).

To further evaluate whether Q2-3 can confer a complementary or additive therapeutic effect on the suppression of tumor metastasis when used in combination with other clinically used anticancer drugs, a study was conducted to assess the effect of Q2-3 plus DT, a drug commonly used for the treatment of human breast cancer, in suppressing the metastatic activities of human MDA-MB-231-Luc2 cells in nude mice. See FIG. 7.

Figure 7B:
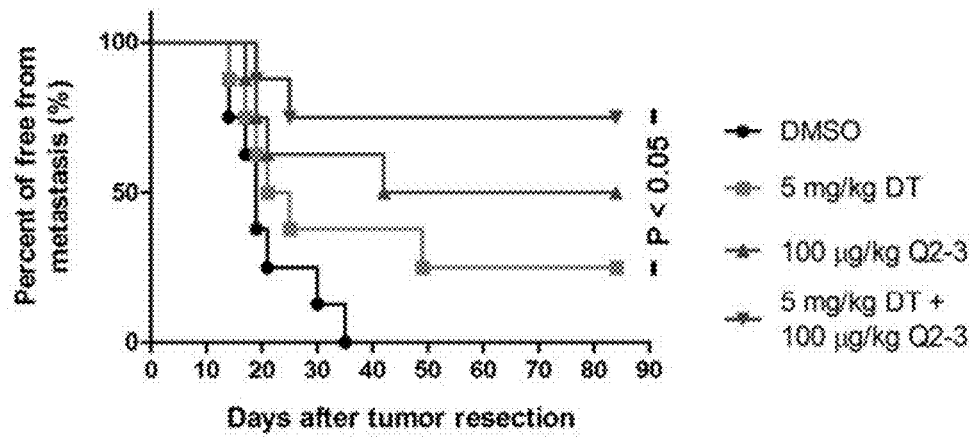
Figure 7C:
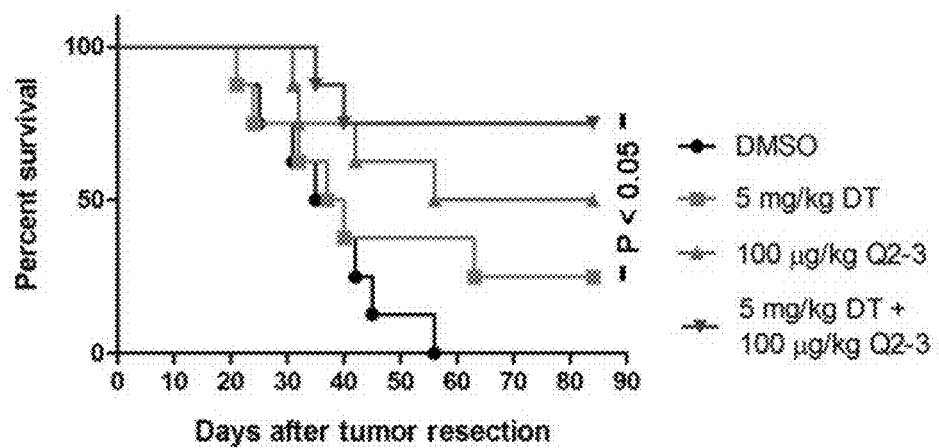

By detecting the luminescent activity of MDA-MB-231-Luc2 cells in test mice after resection of primary mammary tumor tissues in situ (FIG. 7a), it was observed that combination treatment with Q2-3 (100 μg/kg) and DT (5 mg/kg) resulted in substantially higher anti-metastatic activity than treatment with DT only (FIG. 7b). Consistently, this combined treatment also further increased the survival rate of test mice, as compared with those only receiving each single treatment (FIG. 7c). Of note, treatment with low dosage of Q2-3 alone was already more effective than treatment with DT, in terms of suppressing metastasis and prolonging survival; in combination with DT, Q2-3 was even more effective, as shown in FIGS. 7b and 7c.

These results suggest that in vivo administration of Q2-3 could confer strong complementary activity on the therapeutic activity of a clinical anticancer drug, DT, for suppressing metastatic tumor cell activities by regulating the tumor-associated microenvironment.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous to the compounds of this invention also can be made, screened for their modulating activities to opioid receptor and treating opioid receptor associated conditions. Thus, other embodiments are also within the claims.

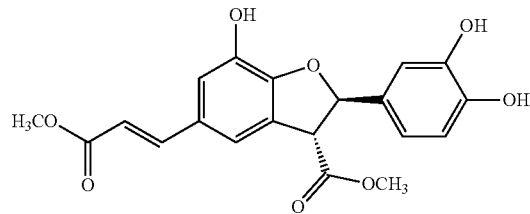

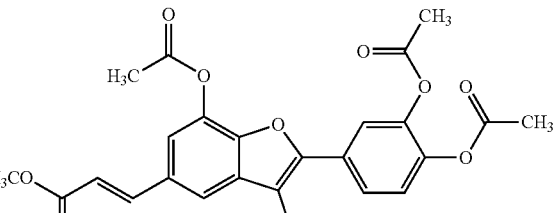

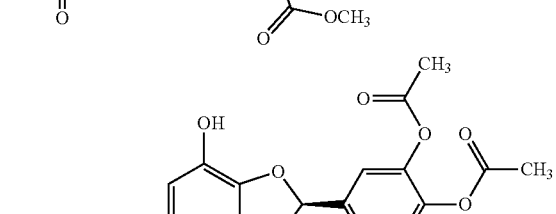

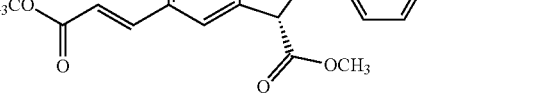

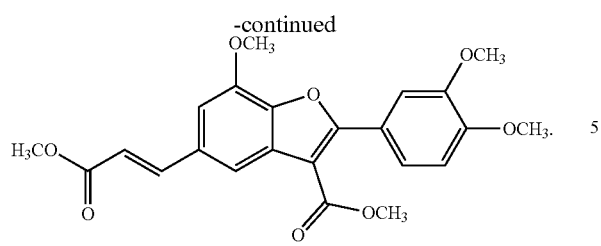
17. The pharmaceutical composition of claim 15, wherein the first compound is docetaxel and the second compound is
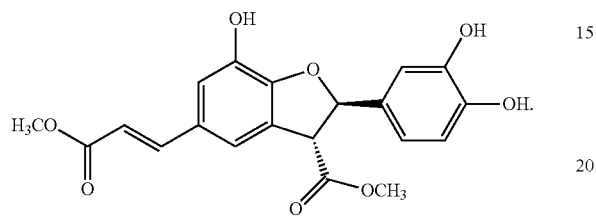

What is claimed is:

1. A method of suppressing tumor metastasis, the method comprising administering to a subject in need thereof an amount of a compound of formula (I):

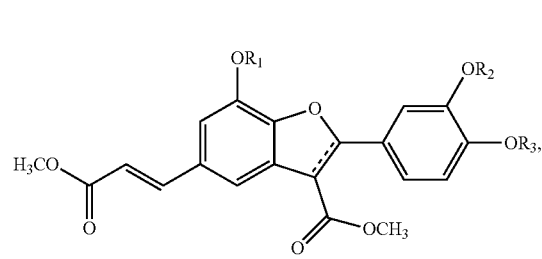

(I)

wherein
each of $R_1$, $R_2$, and $R_3$, independently, is H, $C_{1-6}$ alkyl, or —C(O)$R_4$, $R_4$ being $C_{1-6}$ alkyl, $C_{3-8}$ cycloalkyl, $C_{2-8}$ heterocycloalkyl, $C_{6-14}$ aryl, or $C_{1-13}$ heteroaryl; and --- is a single bond or a double bond, in which the amount is effective to induce secretion of an anti-cancer factor from tumor cells, the anti-cancer factor being interlukin 25 (IL-25), p53, Kangai 1, or nucleoside diphosphate kinase A.

2. The method of claim 1, wherein the anti-cancer factor is IL-25 or p53.

3. The method of claim 1, wherein the anti-cancer factor is IL-25.

4. The method of claim 1, wherein the compound is one of the following compounds:

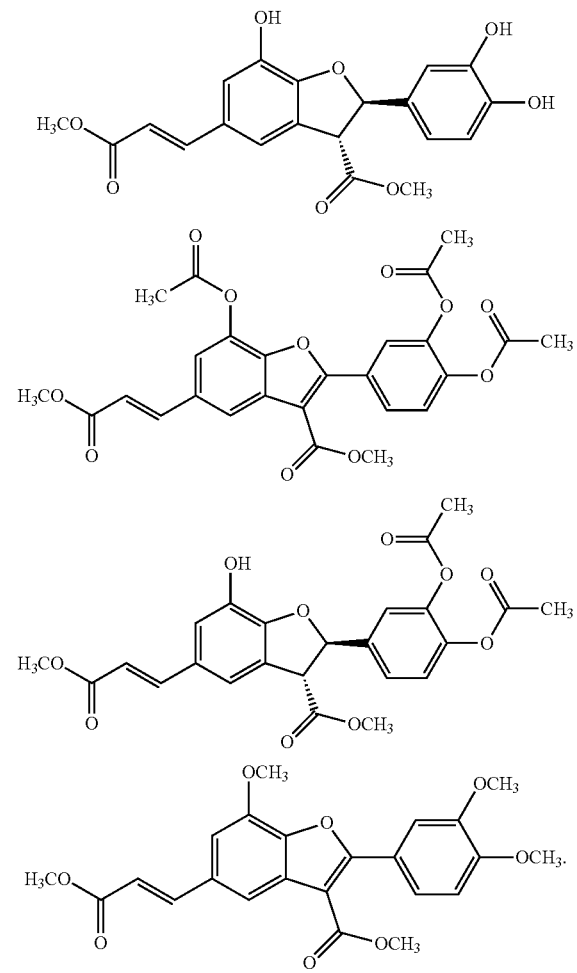

5. The method of claim 1, wherein the compound is

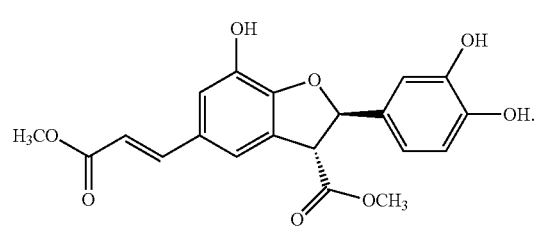

6. A method of treating cancer, the method comprising administering to a subject in need thereof a first amount of a first compound for inhibiting cancer growth and a second amount of a second compound of formula (I):

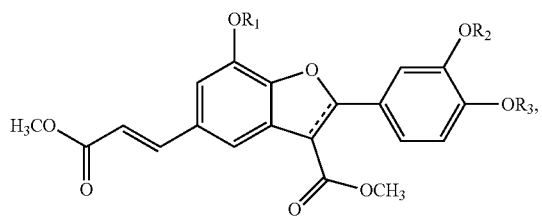

(I)

wherein
each of $R_1$, $R_2$, and $R_3$, independently, is H, $C_{1-6}$ alkyl, or —C(O)$R_4$, $R_4$ being $C_{1-6}$ alkyl, $C_{3-8}$ cycloalkyl, $C_{2-8}$ heterocycloalkyl, $C_{6-14}$ aryl, or $C_{1-13}$ heteroaryl; and --- is a single bond or a double bond,
in which the first amount is effective to inhibit cancer growth and the second amount is effective to suppress cancer metastasis.

7. The method of claim 6, wherein the cancer is breast cancer, non-small cell lung cancer, colorectal cancer, pancreatic cancer, ovarian cancer, skin cancer, prostate cancer, cancer of the brain or nervous system, head and neck cancer, testicular cancer, lung cancer, liver cancer, kidney cancer, bladder cancer, gastrointestinal cancer, bone cancer, cancer of the endocrine system, cancer of the lymphatic system, fibrosarcoma, neurectodermal tumor, mesothelioma, epidermoid carcinoma, or Kaposi's sarcoma.

8. The method of claim 6, wherein the cancer is breast cancer.

9. The method of claim 6, wherein the first compound is selected from the group consisting of Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomyde; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Docetaxel Anhydrous; Doxorubicin; Doxorubicin Hydrochloride; Droloxifene; Droloxifene Citrate; Dromostanolone Propionate; Duazomycin; Edatrexate; Eflomithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Fluorocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-nl; Interferon Alfan3; Interferon Beta-I a; Interferon Gamma-I b; Iproplatin; lrinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Meiphalan; Menogaril; Mercaptopurine; Methotrexate; Methotrexate Sodium; Metoprine; Meturedepa; Mitindomide; Mitocarcin; Mitocromin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Pommer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride, 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminol evulinic acid; amrubicin; amsacrine; anagrelide; anastrozole; andrographolide; angiogenesis inhibitors; antagonist D; antagonist G; antarelix; anti-dorsalizing morphogenetic protein-I; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin I; axinastatin 2; axinastatin 3; azasetron; azatoxin; aza osine; baccatin III derivatives; balanol; batimastat; BCR/ABL antagonists; benzochlorins; benzoylstaurosporine; beta-Iactam derivatives; beta-alethine; beta-clamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecinderivatives; canarypox IL-2; capecitabine; carboxamide-aminotriazole; carboxyamidotriazole; CaRest M3; CARN 700; cartilage derived inhibitor; carzelesin; casein kinase inhibitors (1COS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidenmin B; deslorelin; dexifosfamide; dexrazoxane; dexverapamil; diaziquone; didenmin B; didox; diethylnorspermine; dihydro-5-azacytidine; dihydrotaxol, 9-; dioxamycin; diphenyl spiromustine; docosanol; dolasetron; doxifluridine; droloxifene; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-I receptor inhibitor; interferon agonists; interferons;

interleukins; ioben-guane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatinA; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl-lipidA+myobacterium cell wall sk; mopidamol; multiple drug resistance gene inhibitor; multiple tumor suppressor I-based therapy; mustard anti cancer compound; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetinA; placetin B; plasminogen activator inhibitor; platinum complex; platinum compounds; platinum-triamine complex; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone BI; ruboxyl; safingol; saintopin; SarCNU; sarcophytolA; sargramostim; Sdi I mimetics; semustine; senescence derived inhibitor I; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin I; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer; antimetabolites; platinum-based agents; alkylating agents; tyrosine kinase inhibitors; anthracycline antibiotics; vinca alkaloids; proteasome inhibitors; macrolides; and topoisomerase inhibitors.

10. The method of claim 6, wherein the second compound is one of the following compounds:

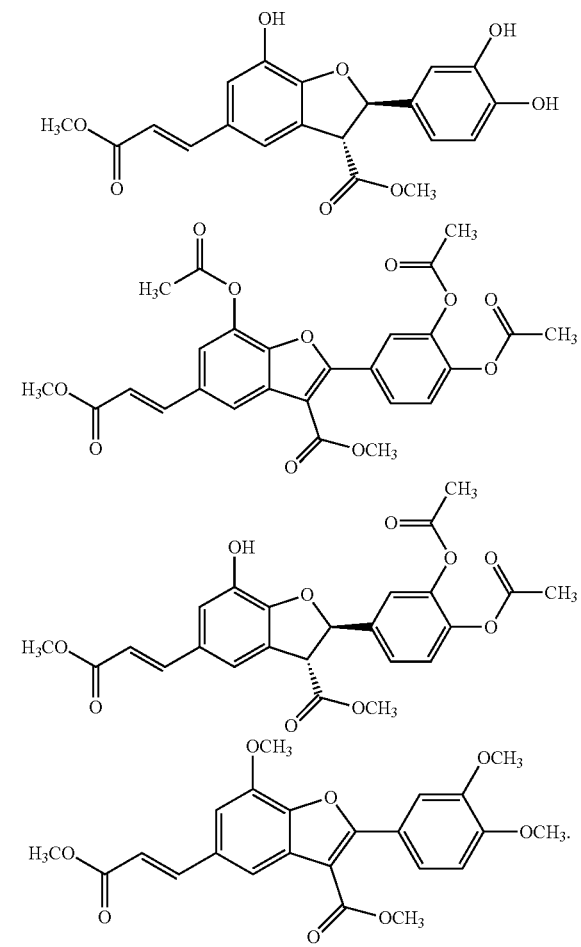

11. The method of claim 6, wherein the first compound is docetaxel and the second compound is

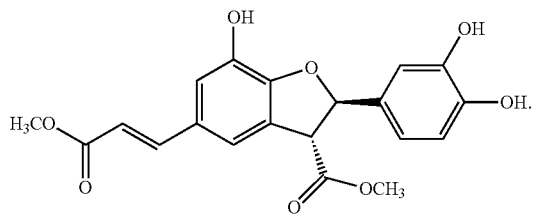 [SMILES: COC(=O)/C=C/c1cc(O)c2c(c1)[C@@H](C(=O)OC)[C@H](c1ccc(O)c(O)c1)O2]

12. A pharmaceutical composition for suppressing tumor metastasis, the pharmaceutical composition comprising a pharmaceutically acceptable carrier and a compound of formula (I):

(I)

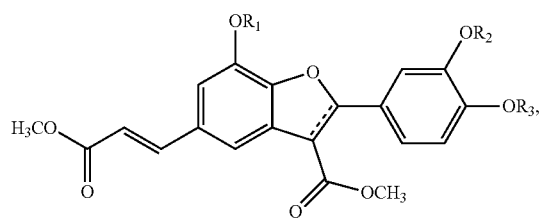

wherein each of $R_1$, $R_2$, and $R_3$, independently, is H, $C_{1-6}$ alkyl, or —C(O)$R_4$, $R_4$ being $C_{1-6}$ alkyl, $C_{3-8}$ cycloalkyl, $C_{2-8}$ heterocycloalkyl, $C_{6-14}$ aryl, or $C_{1-13}$ heteroaryl; and --- is a single bond or a double bond.

13. The pharmaceutical composition of claim 12, wherein the compound is one of the following compounds:

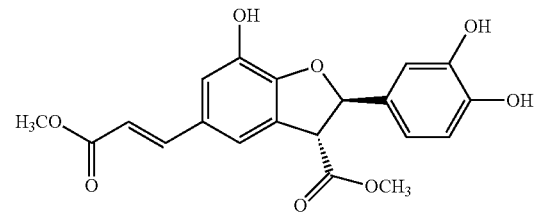 [SMILES: COC(=O)/C=C/c1cc(O)c2c(c1)[C@@H](C(=O)OC)[C@H](c1ccc(O)c(O)c1)O2]

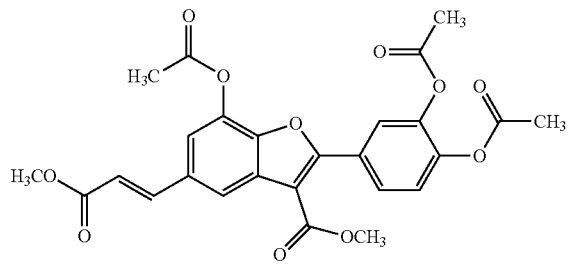

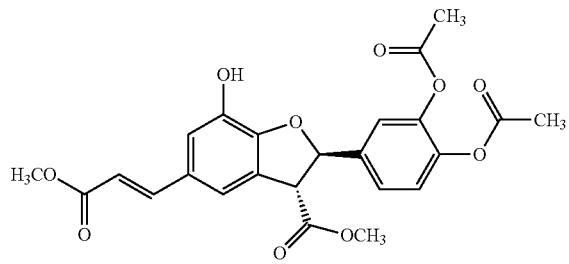

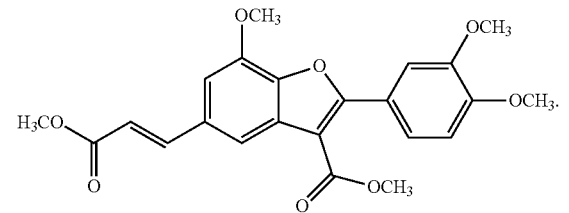

14. The pharmaceutical composition of claim 12, wherein the compound is

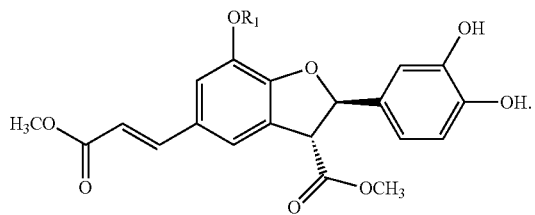

15. A pharmaceutical composition for treating cancer, the pharmaceutical composition comprising a pharmaceutically acceptable carrier, a first compound for inhibiting cancer growth, and a second compound of formula (I):

(I)

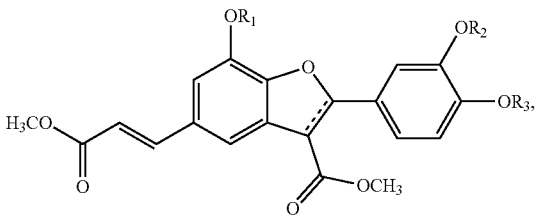

wherein each of $R_1$, $R_2$, and $R_3$, independently, is H, $C_{1-6}$ alkyl, or —C(O)$R_4$, $R_4$ being $C_{1-6}$ alkyl, $C_{3-8}$ cycloalkyl, $C_{2-8}$ heterocycloalkyl, $C_{6-14}$ aryl, or $C_{1-13}$ heteroaryl; and --- is a single bond or a double bond.

16. The pharmaceutical composition of claim 15, wherein the second compound is one of the following compounds: